(12) United States Patent
Palmer et al.

(10) Patent No.: US 10,603,088 B2
(45) Date of Patent: *Mar. 31, 2020

(54) INTERMEDULLARY DEVICES FOR GENERATING AND APPLYING COMPRESSION WITHIN A BODY

(71) Applicant: Arthrex, Inc., Naples, FL (US)

(72) Inventors: Matthew Palmer, Medford, MA (US); Matthew Fonte, Concord, MA (US); Robert Devaney, Auburndale, MA (US)

(73) Assignee: Arthrex, Inc., Naples, FL (US)

( * ) Notice: Subject to any disclaimer, the term of this patent is extended or adjusted under 35 U.S.C. 154(b) by 49 days.

This patent is subject to a terminal disclaimer.

(21) Appl. No.: 15/653,902

(22) Filed: Jul. 19, 2017

(65) Prior Publication Data
US 2017/0319247 A1 Nov. 9, 2017

Related U.S. Application Data

(63) Continuation of application No. 14/541,017, filed on Nov. 13, 2014, now Pat. No. 9,724,138, which is a (Continued)

(51) Int. Cl.
*A61B 17/72* (2006.01)
*A61B 17/00* (2006.01)

(52) U.S. Cl.
CPC ...... *A61B 17/7266* (2013.01); *A61B 17/7291* (2013.01); *A61B 2017/00867* (2013.01); *A61B 2017/00946* (2013.01)

(58) Field of Classification Search
CPC combination set(s) only.
See application file for complete search history.

(56) References Cited

U.S. PATENT DOCUMENTS 3,710,789 A 1/1973 Ersek
4,503,569 A 3/1985 Dotter
(Continued)

FOREIGN PATENT DOCUMENTS

EP 0819413 A2 1/1998
FR 2787313 A1 6/2000

OTHER PUBLICATIONS

ASTM International, Standard Specification and Test Methods for Intramedullary Fixation Devices, 2007.
(Continued)

*Primary Examiner* — Jan Christopher L Merene
(74) *Attorney, Agent, or Firm* — Carlson, Gaskey & Olds, P.C.

(57) ABSTRACT

An intramedullary device includes a central bridge region having a first end and a second end. The intramedullary device also includes a bone engaging feature at both the first end and the second end. At least one of the bone engaging features includes a first barb and a second barb which, in an unbiased condition, flare outwardly from a longitudinal axis of the central bridge region and which are capable of being elastically constrained to a constrained condition such that the first end of the central bridge region may be advanced into a hole in a first bone fragment when the first barb and second barb are elastically constrained. The first barb and second barb are prevented from being withdrawn from the hole in the first bone fragment when the first barb and the second barb are not constrained. The intramedullary device i) is cannulated, ii) generates a compressive load, and iii) comprises nitinol.

27 Claims, 23 Drawing Sheets

Related U.S. Application Data continuation-in-part of application No. 13/624,643, filed on Sep. 21, 2012, now Pat. No. 9,283,006.

(60) Provisional application No. 61/537,766, filed on Sep. 22, 2011, provisional application No. 61/570,091, filed on Dec. 13, 2011, provisional application No. 61/903,820, filed on Nov. 13, 2013.

(56) References Cited

U.S. PATENT DOCUMENTS

| | | | |
|---|---|---|---|
| 4,512,338 | A | 4/1985 | Balko et al. |
| 4,522,200 | A | 6/1985 | Stednitz |
| 4,601,625 | A | 7/1986 | Ernst et al. |
| 4,627,434 | A | 12/1986 | Murray |
| 4,733,665 | A | 3/1988 | Palmaz |
| 4,922,905 | A | 5/1990 | Strecker |
| 4,950,227 | A | 8/1990 | Savin et al. |
| 4,959,065 | A | 9/1990 | Arnett et al. |
| 4,969,888 | A | 11/1990 | Scholten et al. |
| 5,061,275 | A | 10/1991 | Wallsten et al. |
| 5,089,006 | A | 2/1992 | Stiles |
| 5,147,166 | A | 9/1992 | Harker |
| 5,480,447 | A | 1/1996 | Skiba |
| 6,127,597 | A | 10/2000 | Beyar et al. |
| 6,699,247 | B2 | 3/2004 | Zucherman et al. |
| 6,761,731 | B2 | 7/2004 | Majercak |
| 7,261,505 | B2 | 8/2007 | Ernst et al. |
| 7,266,874 | B2 | 9/2007 | Ernst et al. |
| 7,762,751 | B2 | 7/2010 | Panasik et al. |
| 7,875,070 | B2 | 1/2011 | Molaei |
| 7,947,135 | B2 | 5/2011 | Fonte |
| 7,976,648 | B1 | 7/2011 | Boylan et al. |
| 7,985,222 | B2 | 7/2011 | Gall et al. |
| 8,057,147 | B2 | 11/2011 | Ernst et al. |
| 8,062,378 | B2 | 11/2011 | Fonte |
| 8,216,398 | B2 | 7/2012 | Bledsoe et al. |
| 8,394,097 | B2 | 3/2013 | Peyrot et al. |
| 8,404,065 | B2 | 3/2013 | Miller |
| 8,414,583 | B2 | 4/2013 | Prandi et al. |
| 8,425,588 | B2 | 4/2013 | Molaei |
| 8,475,456 | B2 | 7/2013 | Augoyard et al. |
| 8,523,902 | B2 | 9/2013 | Heaven et al. |
| 8,529,601 | B2 | 9/2013 | Green et al. |
| 8,608,785 | B2 | 12/2013 | Reed et al. |
| 8,715,325 | B2 | 5/2014 | Weiner et al. |
| 8,721,646 | B2 | 5/2014 | Fox |
| 8,764,842 | B2 | 7/2014 | Graham |
| 8,834,483 | B2 | 9/2014 | Cheney et al. |
| D720,072 | S | 12/2014 | Cheney et al. |
| 9,017,331 | B2 | 4/2015 | Fox |
| D745,163 | S | 12/2015 | Cheney et al. |
| 9,282,977 | B2* | 3/2016 | Penzimer ........... A61B 17/8875 |
| 9,339,268 | B2 | 5/2016 | Fox |
| 9,757,168 | B2* | 9/2017 | Seavey ............. A61B 17/7291 |
| 10,098,676 | B2* | 10/2018 | Girod .................... A61B 17/68 |
| 2002/0032444 | A1 | 3/2002 | Mische |
| 2002/0068939 | A1 | 6/2002 | Levy et al. |
| 2003/0069645 | A1 | 4/2003 | Ball et al. |
| 2004/0220678 | A1 | 11/2004 | Chow et al. |
| 2005/0187555 | A1* | 8/2005 | Biedermann .......... A61B 17/68 606/62 |
| 2005/0240190 | A1 | 10/2005 | Gall et al. |
| 2008/0132894 | A1 | 6/2008 | Coilard-Lavirotte et al. |
| 2008/0177262 | A1 | 7/2008 | Augoyard et al. |
| 2008/0221697 | A1 | 9/2008 | Graser |
| 2008/0269745 | A1 | 10/2008 | Justin |
| 2008/0269746 | A1 | 10/2008 | Justin |
| 2008/0269747 | A1 | 10/2008 | Justin |
| 2008/0269748 | A1 | 10/2008 | Justin et al. |
| 2008/0269750 | A1 | 10/2008 | Justin |
| 2008/0269808 | A1 | 10/2008 | Gall et al. |
| 2009/0182336 | A1 | 7/2009 | Brenzel et al. |
| 2010/0131014 | A1 | 5/2010 | Peyrot et al. |
| 2010/0241120 | A1 | 9/2010 | Bledsoe et al. |
| 2011/0004212 | A1 | 1/2011 | Gall et al. |
| 2011/0144644 | A1 | 6/2011 | Prandi et al. |
| 2011/0301653 | A1 | 12/2011 | Reed et al. |
| 2012/0083791 | A1* | 4/2012 | Cheney ............. A61B 17/8872 606/99 |
| 2013/0046390 | A1 | 2/2013 | Rabiner et al. |
| 2013/0066435 | A1 | 3/2013 | Averous et al. |
| 2013/0123785 | A1 | 5/2013 | Fonte |
| 2013/0131822 | A1 | 5/2013 | Lewis et al. |
| 2013/0253515 | A1 | 9/2013 | Augoyard et al. |
| 2013/0253597 | A1 | 9/2013 | Augoyard et al. |
| 2013/0274746 | A1 | 10/2013 | Peyrot et al. |
| 2014/0039630 | A1 | 2/2014 | Peyrot et al. |
| 2014/0142715 | A1 | 5/2014 | McCormick |
| 2014/0257420 | A1 | 9/2014 | Fox |
| 2014/0324048 | A1 | 10/2014 | Fox |
| 2015/0134016 | A1 | 5/2015 | Biedermann et al. |
| 2015/0141994 | A1 | 5/2015 | Cheney et al. |
| 2015/0223848 | A1 | 8/2015 | McCormick |
| 2015/0320460 | A1 | 11/2015 | Taber et al. |
| 2015/0351815 | A1 | 12/2015 | Wales et al. |
| 2016/0081728 | A1 | 3/2016 | McCormick |

OTHER PUBLICATIONS

Bong et al., Intramedullary Nailing of the Lower Extremity: Biomechanics and Biology, Journal of the American Academy of Orthopaedic Surgeons, vol. 15, No. 2, Feb. 2007, pp. 97-106.

Cai et al., Texture Evolution During Nitinol Martensite Detwinning and Phase Transformation, Applied Physics Letters, 2013, 103, 241909, AIP Publishing LLC.

Duerig et al., Overview of Superelastic Stent Design, Min Invas Ther & Allied Technol, 2000, pp. 235-246, 9(3/4).

Gruszka et al., The Durability of the Intrascaphoid Compression of Headless Compression Screws: In Vitro Study, The Journal of Hand Surgery, Jun. 2012, 37(6), pp. 1142-1150.

Huang et al., Ion Release from NiTi Orthodontic Wires in Artificial Saliva with Various Acidities, Biomaterials, 2003, pp. 3585-3592, 24(20).

Kujala et al., Bone Modeling Controlled by a Nickel-Titanium Shape Memory Alloy Intramedullary Nail, Biomaterials 23, 2002, pp. 2535-2543.

Stoeckel et al., A Survey of Stent Designs, Min Invas Ther & Allied Technol, 2002, pp. 137-147, 11(4).

Synthes, Synthes Titanium Intramedullary Nails Comprehensive Product Range, Original Instruments and Implants of the Association for the Study of Internal Fixation—AO ASIF, 2003.

* cited by examiner

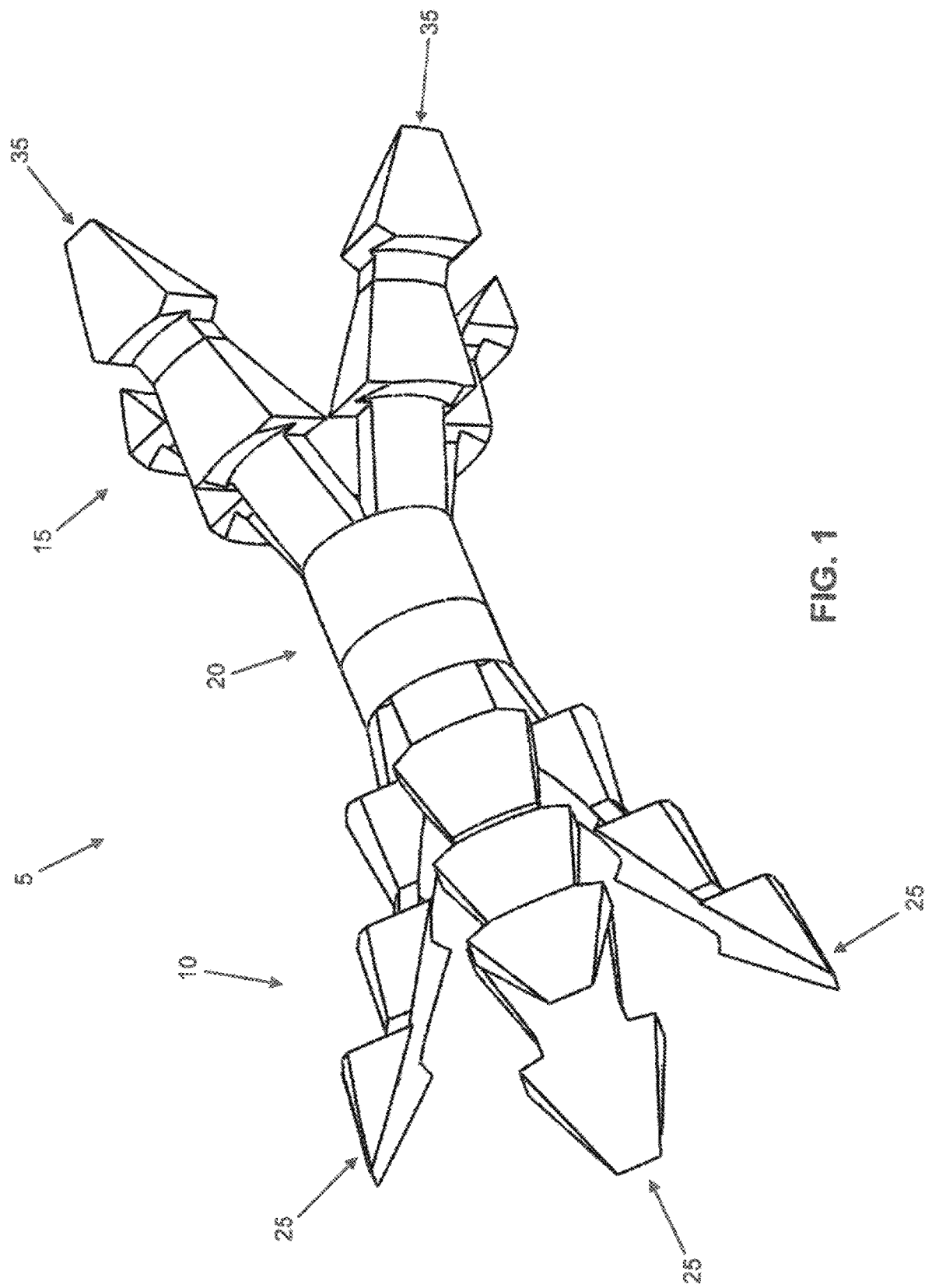

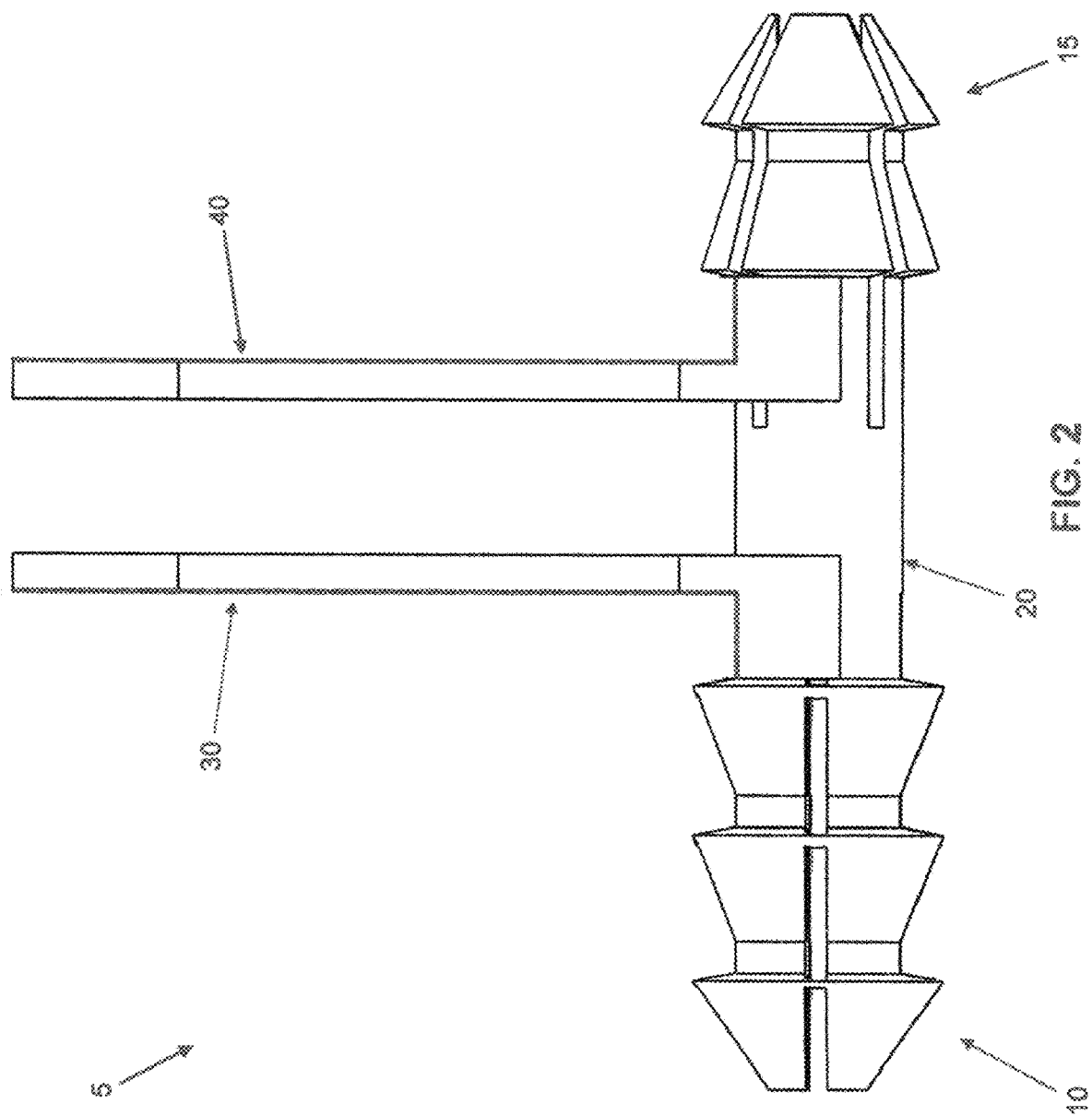

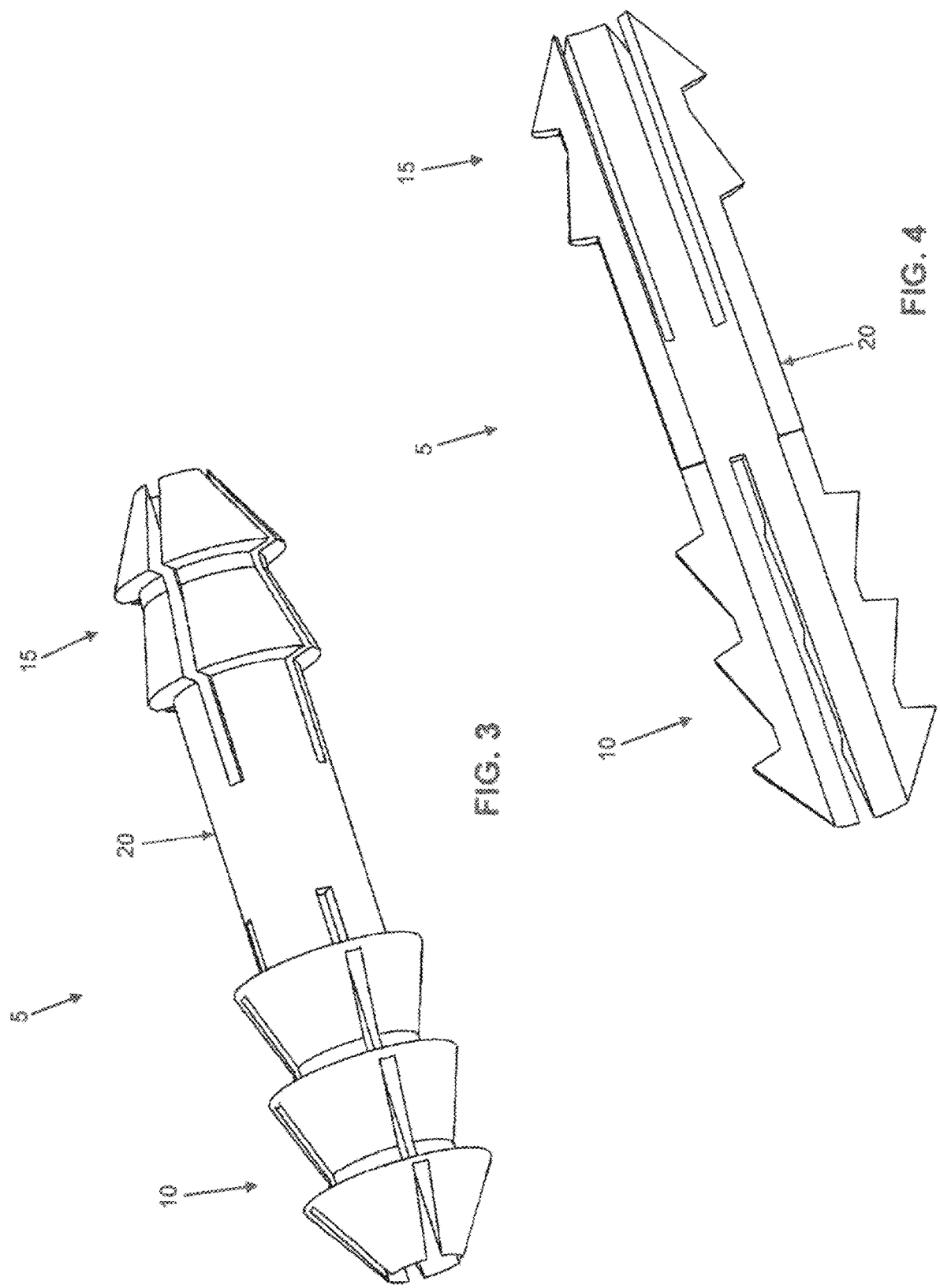

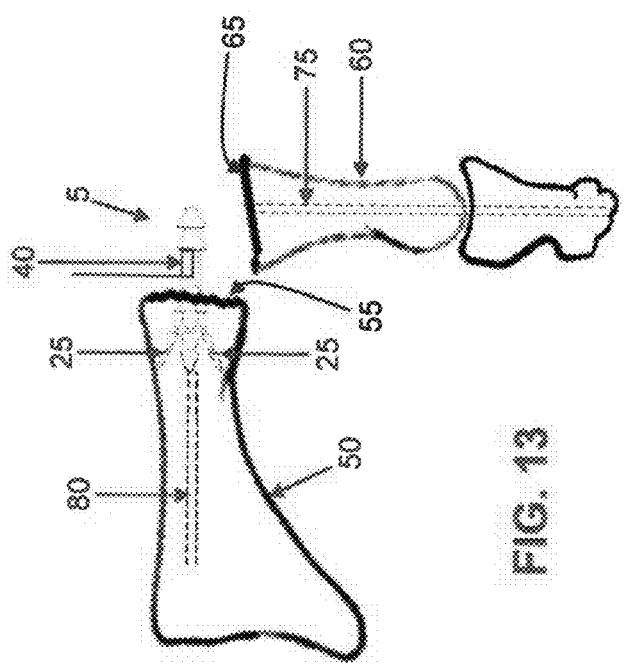
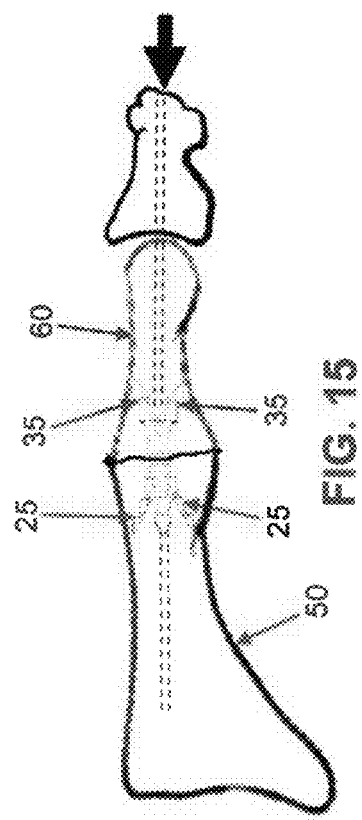
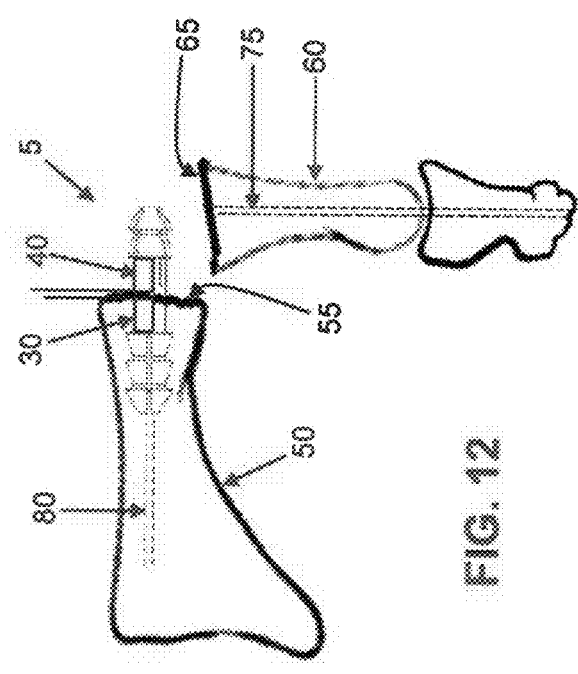
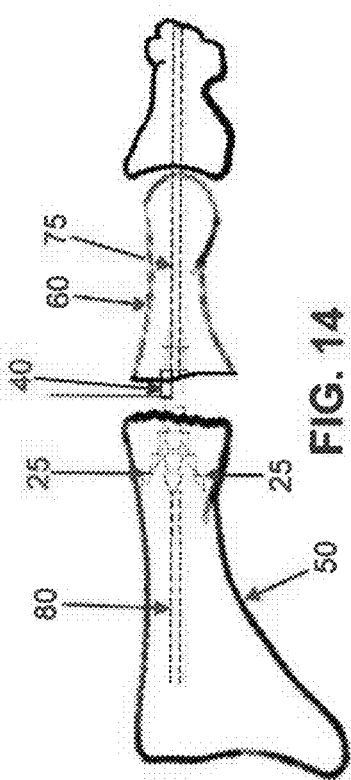

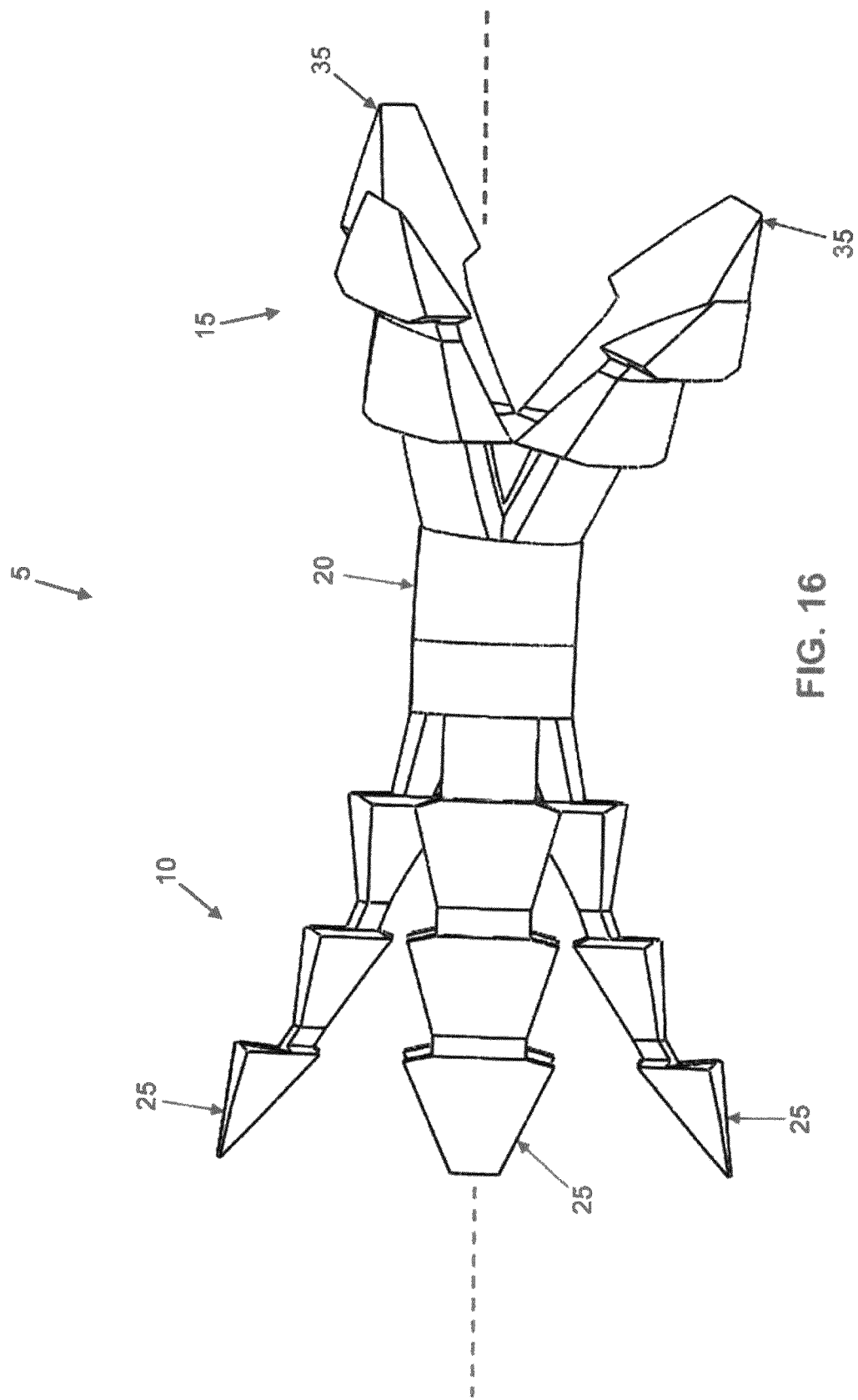

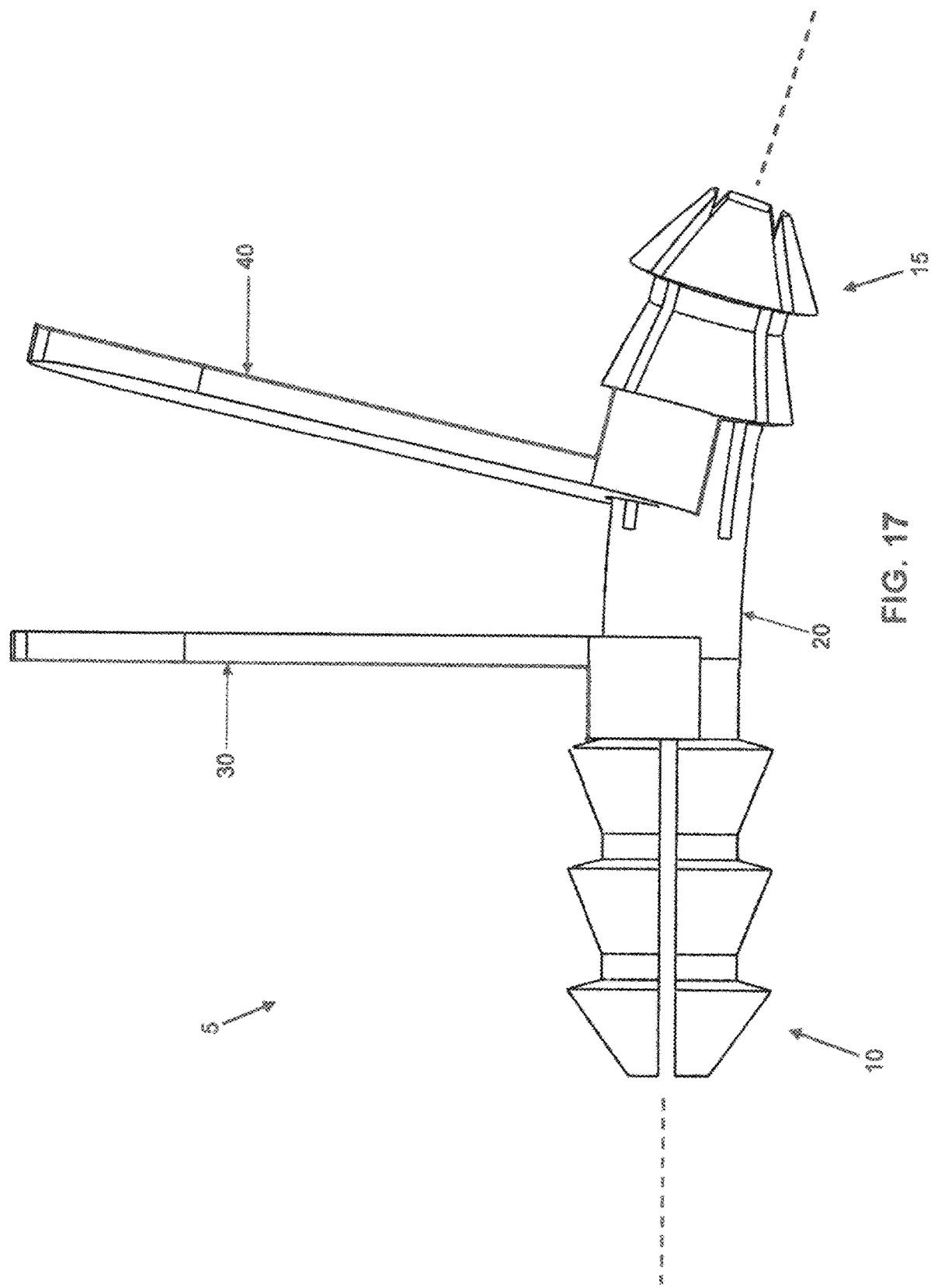

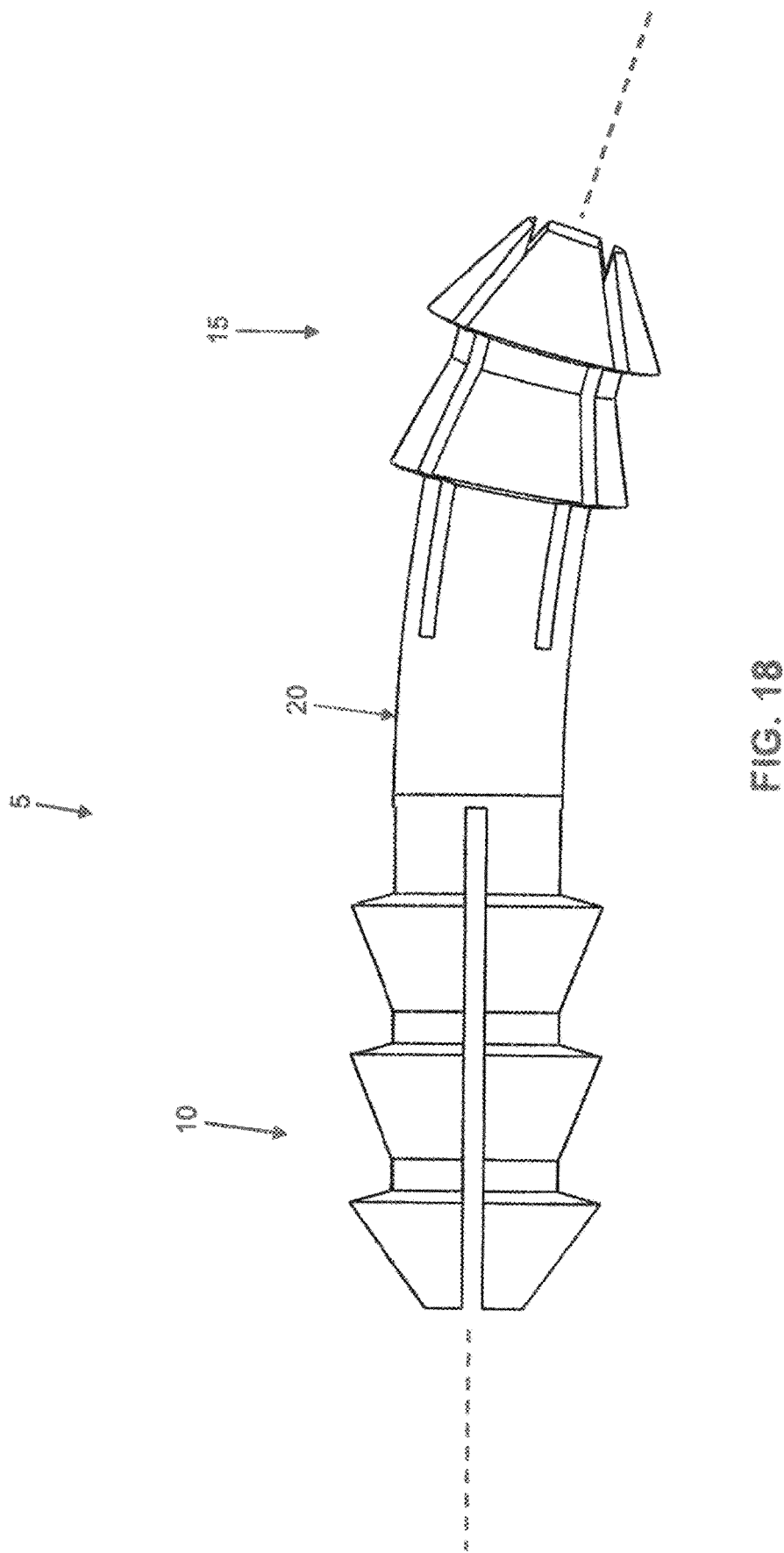

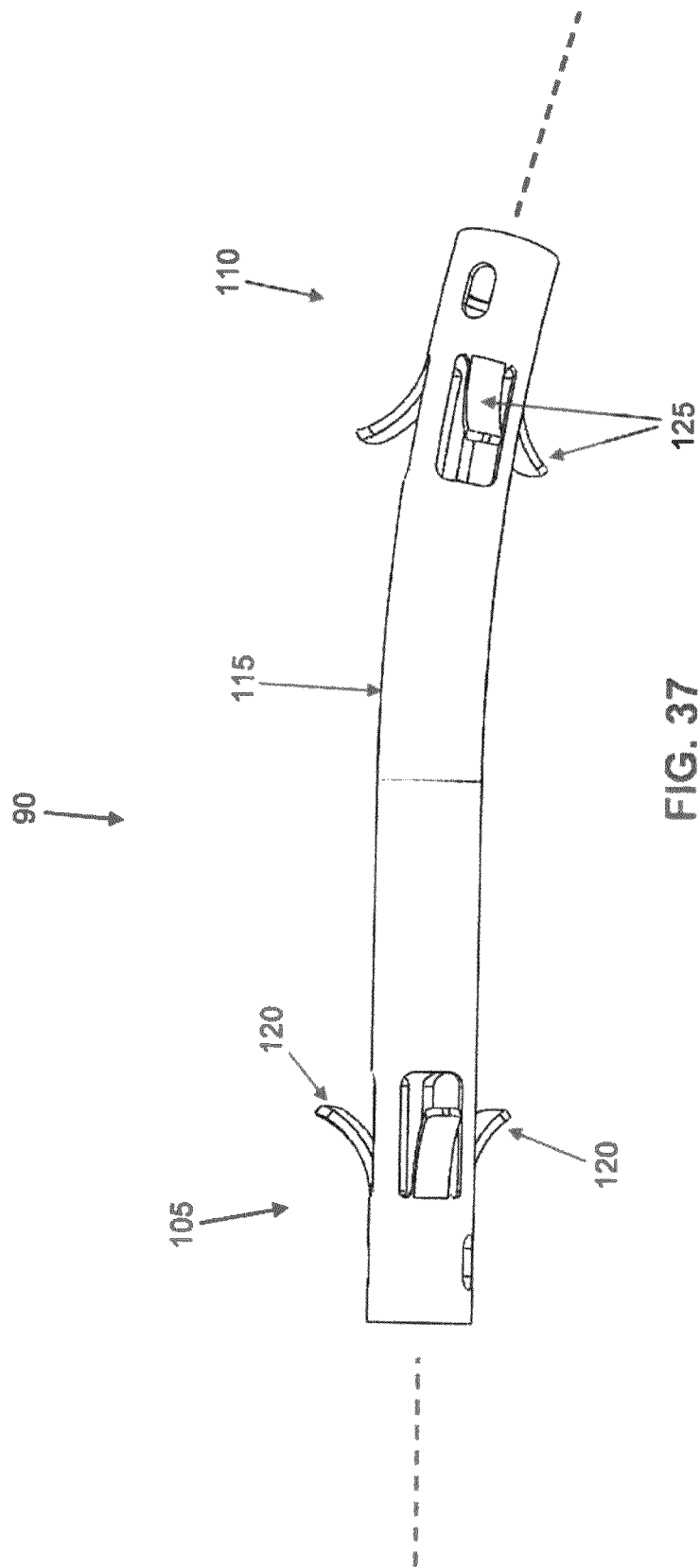

INTERMEDULLARY DEVICES FOR GENERATING AND APPLYING COMPRESSION WITHIN A BODY

REFERENCE TO PENDING PRIOR PATENT APPLICATIONS

This patent application is a continuation of U.S. patent application Ser. No. 14/541,017, filed Nov. 13, 2014, now U.S. Pat. No. 9,724,138 granted on Aug. 8, 2017, which is a continuation-in-part of U.S. patent application Ser. No. 13/624,643, filed Sep. 21, 2012, now U.S. Pat. No. 9,283,066 granted on Mar. 15, 2016, which claims the benefit of prior U.S. Provisional Patent Application Ser. No. 61/537,766, filed Sep. 22, 2011, and U.S. Provisional Patent Application Ser. No. 61/570,091, filed Dec. 13, 2011. U.S. application Ser. No. 14/541,017 claims priority to U.S. Provisional Patent Application Ser. No. 61/903,820 filed Nov. 13, 2013.

FIELD OF THE INVENTION

The present invention relates to devices and methods for generating, applying, and maintaining compression to a site in a human or animal body in order to effect healing of diseased or damaged tissue. The invention finds particular utility in the field of orthopedics and specifically for generating and maintaining compression between bone fragments that are to be fused. While the invention has application throughout the body, its utility will be illustrated herein in the context of the repair of injured bone tissue, such as the proximal and distal interphalangeal joint of the second, third, or fourth toe and/or fingers. Additionally, the invention has application to aid in the fusion of broken ribs, etc.

BACKGROUND OF THE INVENTION

In the field of orthopedic surgery it is common to rejoin broken bones. The success of the surgical procedure often depends on the successful re-approximation of the bone fragments, the amount of compression achieved between the bone fragments, and the ability to maintain that compression between the bone fragments. If the surgeon is unable to bring the bone fragments into close contact, a gap will exist between the bone fragments and the bone tissue will need to fill that gap before complete healing can take place. Furthermore, gaps between bone fragments that are too large allow motion to occur between the bone fragments, disrupting the healing tissue and thus slowing the healing process. Optimal healing requires that the bone fragments be in close contact with each other, and for a compressive load to be applied and maintained between the bone fragments. Compressive strain between bone fragments has been found to accelerate the healing process in accordance with Wolf's Law.

Broken bones can be rejoined using screws, staples, plates, pins, intramedullary devices, and other devices known in the art. These devices are designed to assist the surgeon with reducing the fracture and creating a compressive load between the bone fragments. Intramedullary devices are often used for fractures of the long bones; however, they are also frequently used in the phalanges and specifically for the treatment of "hammer toe", which is a deformity of the proximal interphalangeal joint of the second, third, or fourth toe causing the toe to be permanently bent. Typical intramedullary devices used in the phalanges have opposing ends that are adapted to grip against the wall of the intramedullary canal. These intramedullary devices are typically made of titanium alloys, stainless steel alloys, Nitinol and other materials, e.g., PEEK. The titanium alloy devices and stainless steel alloy devices often have barbs or threaded regions at their opposing ends to grip the wall of the intramedullary canal. The Nitinol devices typically have a pair of radially extending "legs" at their opposing ends that expand outward when warmed to body temperature, with the pair of legs at each end being disposed in a common plane.

While these intramedullary devices are designed to bring the bone fragments into close contact and to generate a compressive load between the bone fragments, these devices do not always succeed in accomplishing this objective. It is widely reported that the compressive load dissipates rapidly as the bone relaxes and remodels. Furthermore, gripping the bone with only a pair of co-planar legs does not provide significant torsional stability to the fusion site.

Thus there exists a clinical need for intramedullary devices that are better able to bring bone fragments into close proximity with each other, generate a compressive load, and maintain that compressive load for a prolonged period of time while healing occurs.

SUMMARY OF THE INVENTION

The present invention comprises the provision and use of novel intramedullary devices that are better able to bring bone fragments into close proximity with each other, generate a compressive load, and maintain that compressive load for a prolonged period of time while healing occurs.

In one preferred form of the invention, there is provided apparatus for securing a first bone fragment to a second bone fragment, the apparatus comprising: a fusion device, the fusion device comprising: a shaft having a first end and a second end; a first bone-engaging feature formed on the shaft at a first location, the first bone-engaging feature comprising at least one barb which, in its unbiased condition, flares outwardly from the longitudinal axis of the shaft and which is capable of being elastically constrained to a position substantially parallel to the longitudinal axis of the shaft, such that the first end of the shaft may be advanced into a hole in the first bone fragment when the at least one barb is elastically constrained to a position substantially parallel to the longitudinal axis of the shaft but is prevented from being withdrawn from the hole in the first bone fragment when the at least one barb is in its unbiased condition; and a second bone-engaging feature formed on the shaft at a second location, the second bone-engaging feature comprising at least one barb which, in its unbiased condition, flares outwardly from the longitudinal axis of the shaft and which is capable of being elastically constrained to a position substantially parallel to the longitudinal axis of the shaft, such that the second end of the shaft may be advanced into a hole in the second bone fragment when the at least one barb is elastically constrained to a position substantially parallel to the longitudinal axis of the shaft, but is prevented from being withdrawn from the hole in the second bone fragment when the at least one barb is in its unbiased condition.

In another preferred form of the invention, there is provided a method for securing a first bone fragment to a second bone fragment, the method comprising: providing a fusion device, the fusion device comprising: a shaft having a first end and a second end; a first bone-engaging feature formed on the shaft at a first location, the first bone-engaging feature comprising at least one barb which, in its unbiased condition, flares outwardly from the longitudinal axis of the shaft and which is capable of being elastically constrained to a position substantially parallel to the longitudinal axis of the shaft, such that the first end of the shaft may be advanced into a hole in the first bone fragment when the at least one barb is elastically constrained to a position substantially parallel to the longitudinal axis of the shaft but is prevented from being withdrawn from the hole in the first bone fragment when the at least one barb is in its unbiased condition; and a second bone-engaging feature formed on the shaft at a second location, the second bone-engaging feature comprising at least one barb which, in its unbiased condition, flares outwardly from the longitudinal axis of the shaft and which is capable of being elastically constrained to a position substantially parallel to the longitudinal axis of the shaft, such that the second end of the shaft may be advanced into a hole in the second bone fragment when the at least one barb is elastically constrained to a position substantially parallel to the longitudinal axis of the shaft but is prevented from being withdrawn from the hole in the second bone fragment when the at least one barb is in its unbiased condition; elastically constraining the at least one barb of the first bone-engaging feature to a position substantially parallel to the longitudinal axis of the shaft, and elastically constraining the at least one barb of the second bone-engaging feature to a position substantially parallel to the longitudinal axis of the shaft; advancing the first bone-engaging feature into a hole in the first bone fragment, and advancing the second bone-engaging feature into a hole in the second bone fragment; and releasing the constraint on the at least one barb of the first bone-engaging feature and releasing the constraint on the at least one barb of the second bone-engaging feature, whereby to generate and maintain compression between the first bone fragment and the second bone fragment.

In another preferred form of the invention, there is provided apparatus for securing a first bone fragment to a second bone fragment, the apparatus comprising: a fusion device, the fusion device comprising: a shaft having a first end and a second end; a first bone-engaging feature formed on the shaft at a first location, the first bone-engaging feature comprising at least one barb which, in its unbiased condition, flares outwardly from the longitudinal axis of the shaft and which is capable of being elastically constrained to a position substantially parallel to the longitudinal axis of the shaft, the at least one barb being configured so that the first end of the shaft may be advanced into a hole in the first bone fragment but prevents the first end of the shaft from being withdrawn from the hole in the first bone fragment; and a second bone-engaging feature formed on the shaft at a second location, the second bone-engaging feature comprising at least one barb which, in its unbiased condition, flares outwardly from the longitudinal axis of the shaft and which is capable of being elastically constrained to a position substantially parallel to the longitudinal axis of the shaft, the at least one barb being configured so that the second end of the shaft may be advanced into a hole formed in the second bone fragment but prevents the second end of the shaft from being withdrawn from the hole in the second bone fragment; wherein at least a portion of the shaft disposed between the first bone-engaging feature and the second bone-engaging feature is capable of being elastically stretched; and a holding element connectable to the fusion device for releasably holding the at least a portion of the shaft in a stretched condition.

In another preferred form of the invention, there is provided a method for securing a first bone fragment to a second bone fragment, the method comprising: providing a fusion device, the fusion device comprising: a shaft having a first end and a second end; a first bone-engaging feature formed on the shaft at a first location, the first bone-engaging feature comprising at least one barb which, in its unbiased condition, flares outwardly from the longitudinal axis of the shaft and which is capable of being elastically constrained to a position substantially parallel to the longitudinal axis of the shaft, the at least one barb being configured so that the first end of the shaft may be advanced into a hole in the first bone fragment but prevents the first end of the shaft from being withdrawn from the hole in the first bone fragment; and a second bone-engaging feature formed on the shaft at a second location, the second bone-engaging feature comprising at least one barb which, in its unbiased condition, flares outwardly from the longitudinal axis of the shaft and which is capable of being elastically constrained to a position substantially parallel to the longitudinal axis of the shaft, the at least one barb being configured so that the second end of the shaft may be advanced into a hole formed in the second bone fragment but prevents the second end of the shaft from being withdrawn from the hole in the second bone fragment; wherein at least a portion of the shaft disposed between the first bone-engaging feature and the second bone-engaging feature is capable of being elastically stretched; longitudinally stretching the fusion device so that the fusion device is in a longitudinally stretched condition; holding the fusion device in its longitudinally stretched condition; inserting the fusion device into a hole in the first bone fragment while the fusion device is in its longitudinally stretched condition, and inserting the fusion device into a hole in the second bone fragment while the fusion device is in its longitudinally stretched condition; and releasing the fusion device from its longitudinally stretched condition so as to apply compression between the first bone fragment and the second bone fragment.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 1-4 are schematic views showing an intramedullary fusion device formed in accordance with the present invention;

FIGS. 5-15 are schematic views showing the novel intramedullary fusion device of FIGS. 1-4 being used to treat a hammer toe condition;

FIGS. 16-18 are schematic views showing another intramedullary fusion device formed in accordance with the present invention;

FIG. 37 is a schematic view showing another intramedullary fusion device formed in accordance with the present invention and which may be used with the intramedullary fusion system shown in FIGS. 19-25.

DETAILED DESCRIPTION OF THE PREFERRED EMBODIMENTS

Figure 4A:
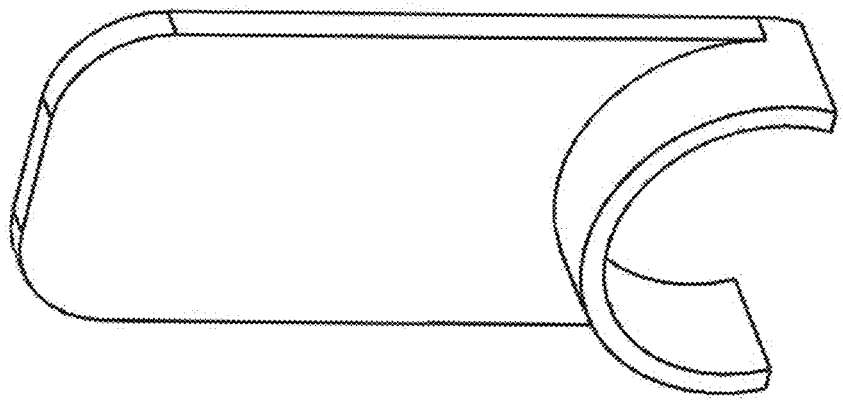
FIG. 4A is a schematic view showing removable retaining tabs which may be used to hold the first and second barbed end regions of the intramedullary fusion device of FIGS. 1-4 in their radially constrained condition.

The present invention comprises the provision and use of novel intramedullary devices that are better able to bring bone fragments into close proximity with each other, generate a compressive load, and maintain that compressive load for a prolonged period of time while healing occurs.

Looking first at FIGS. 1-4, there is shown an intermedullary fusion device 5 manufactured from a shape memory material (e.g., a material capable of exhibiting superelasticity and/or a temperature-induced shape change). The shape memory material may be a metal alloy (e.g., Nitinol) or a polymer (e.g., appropriately processed PEEK). Intramedullary fusion device 5 comprises a first barbed end region 10, a second barbed end region 15, and a central bridge region 20 connecting first barbed end region 10 to second barbed end region 15. Intramedullary fusion device 5 is preferably cannulated so as to allow the intramedullary fusion device to be installed over a k-wire if desired, while also allowing a k-wire to be passed through the intramedullary fusion device following implantation if the surgeon desires to fuse a distal or proximal joint. The first and second barbed regions flare outward in multiple planes, preferably engaging the surrounding bone about the full circumference of the intramedullary fusion device, thereby providing excellent torsional stability to the fusion site.

First barbed end region 10 comprises a plurality of barbs 25 which, in their unbiased condition, flare outward from the longitudinal axis of intramedullary fusion device 5 in the manner shown in FIG. 1. The flare may increase linearly over the length of the barb, or it may increase non-linearly over the length of the barb to enable first barbed end region 10 to better engage the "hourglass-shaped" intramedullary canal. The better that first barbed end region 10 engages the intramedullary canal, the more even the pressure distribution will be. However, barbs 25 can be strained to a position parallel to the longitudinal axis of intramedullary fusion device 5 and constrained in that position (e.g., via a removable retaining tab 30, FIGS. 2 and 4A) so as to reduce the cross-sectional profile of first barbed end region 10, whereby to allow for insertion into a drilled hole in bone, as will hereinafter be discussed. Barbs 25 can be constrained in a state where they partially occupy the cannulation of intramedullary fusion device 5 (i.e., where barbs 25 are strained to a point past parallel to the longitudinal axis of intramedullary fusion device 5), thereby further reducing the cross-sectional area of first barbed end region 10. This is beneficial for accessing the intramedullary canal through a small drilled hole. Each of the barbs 25 include a plurality of barbed segments. As shown in FIG. 2, the removable retaining tab 30 partially surrounds a circumference of the barbs 25 when in the constrained condition.

While FIG. 1 illustrates a device with four barbs 25 on first barbed end region 10, it should be appreciated that first barbed end region 10 can be made with more or fewer barbs. Upon removing retaining tab 30, barbs 25 are allowed to flare outward again, whereby to grip the side wall of the drilled hole and intramedullary canal receiving first barbed end region 10, whereby to lock first barbed end region 10 to a bone fragment via an expansive force on the intramedullary canal, as will also hereinafter be discussed.

In one preferred form of the invention, barbs 25 of first barbed end region 10 are separated from one another by relatively small longitudinal gaps when barbs 25 are strained to a position parallel to the longitudinal axis of intramedullary fusion device 5, such that barbs 25 collectively provide a substantially full circumferential structure for first barbed end region 10 (i.e., when barbs 25 are strained to a position parallel to the longitudinal axis of intramedullary fusion device 5, barbs 25 collectively provide a substantially continuous extension of central bridge region 20 of intramedullary fusion device 5). See FIGS. 3 and 4.

Second barbed end region 15 comprises a plurality of barbs 35 which, in their unbiased condition, flare outward from the longitudinal axis of intramedullary fusion device 5 in the manner shown in FIG. 1. The flare may increase linearly over the length of the barb, or it may increase non-linearly over the length of the barb to enable second barbed end region 15 to better engage the "hourglass-shaped" intramedullary canal. The better that second barbed end region 15 engages the intramedullary canal, the more even the pressure distribution will be. However, barbs 35 can be strained to a position parallel to the longitudinal axis of intramedullary fusion device 5 and constrained in that position (e.g., via a removable retaining tab 40, FIGS. 2 and 4A) so as to reduce the cross-sectional profile of second barbed end region 15, whereby to allow for insertion into a drilled hole in bone, as will hereinafter be discussed. Barbs 35 can be constrained in a state where they partially occupy the cannulation of intramedullary fusion device 5 (i.e., where barbs 35 are constrained to a point past parallel to the longitudinal axis of intramedullary fusion device 5), thereby further reducing the cross-sectional area of second barbed region 15. This is beneficial for accessing the intramedullary canal through a small drilled hole. Each of the barbs 35 include a plurality of barbed segments. As shown in FIG. 2, the removable retaining tab 40 partially surrounds a circumference of the barbs 35 when in the constrained condition.

While FIG. 1 illustrates a device with four barbs 35 on the second barbed end region 15, it should be appreciated that second barbed end region 15 can be made with more or fewer barbs. Upon removing retaining tab 40, barbs 35 are allowed to flare outward, whereby to grip the side wall of the drilled hole and intramedullary canal receiving second barbed end region 15, whereby to lock second barbed end region 15 to a bone fragment via an expansive force on the intramedullary canal, as will also hereinafter be discussed.

In one preferred form of the invention, barbs 35 of second barbed end region 15 are separated from one another by relatively small longitudinal gaps when barbs 35 are strained to a position parallel to the longitudinal axis of intramedullary fusion device 5, such that barbs 35 collectively provide a substantially full circumferential structure for second barbed end region 15 (i.e., when barbs 35 are strained to a position parallel to the longitudinal axis of intramedullary fusion device 5, barbs 35 collectively provide a substantially continuous extension of central bridge region 20 of intramedullary fusion device 5). See FIGS. 3 and 4.

It should be appreciated that first barbed end region 10 and second barbed end region 15 may have different numbers of barbs, e.g., first barbed end region 10 may comprise four barbs 25 and second barbed end region 15 may comprise three barbs 35. However, it should be appreciated that regardless of the number of barbs 25 provided on first barbed end region 10, and regardless of the number of barbs 35 provided on second barbed end region 15, the barbs 25 of first barbed end region 10 preferably engage the surrounding bone about the full circumference of the intramedullary fusion device, and the barbs 35 of second barbed end region 15 preferably engage the surrounding bone about the full circumference of the intramedullary fusion device.

Central bridge region 20 preferably comprises a generally cylindrical shape and is preferably sized so as to have an outer diameter somewhat less than the major diameters of first barbed end region 10 and second barbed end region 15 when their barbs 25, 35, respectively, have been strained to a position parallel to the longitudinal axis of intramedullary fusion device 5.

Figure 5:
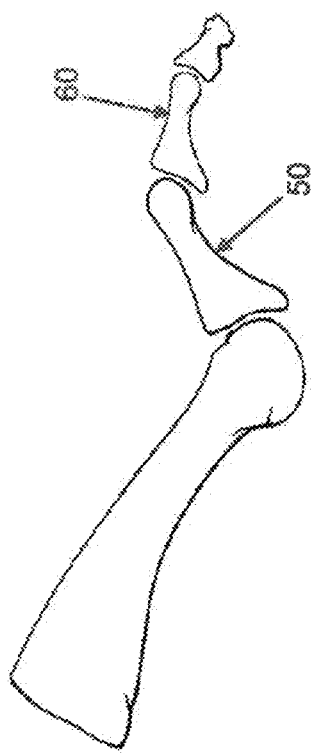

Intramedullary fusion device 5 may be used to secure together two bone fragments under compression. By way of example but not limitation, and looking now at FIGS. 5-15, intramedullary fusion device 5 may be used to treat a hammer toe deformity (FIG. 5).

Figure 6:
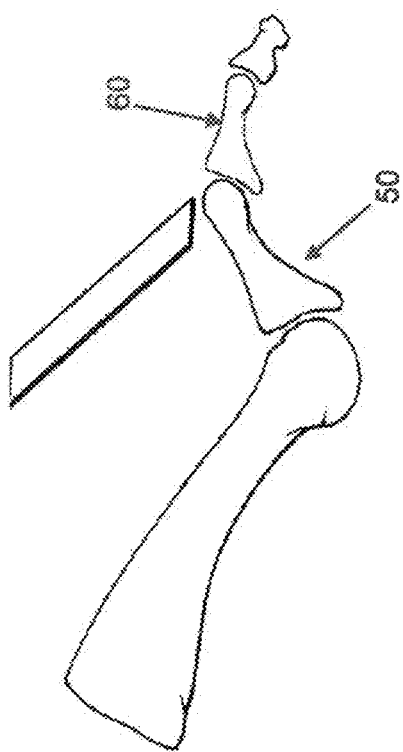
Figure 7:
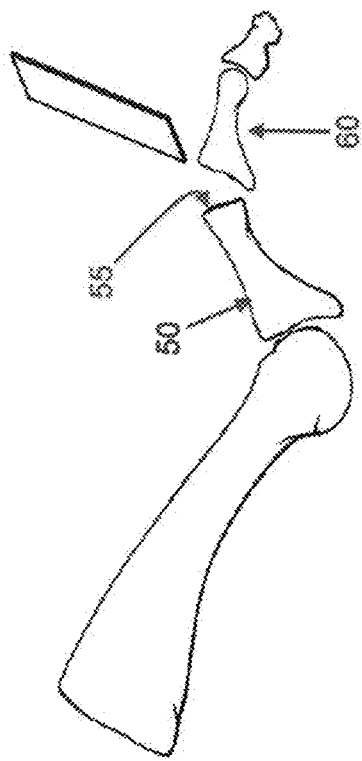
Figure 8:
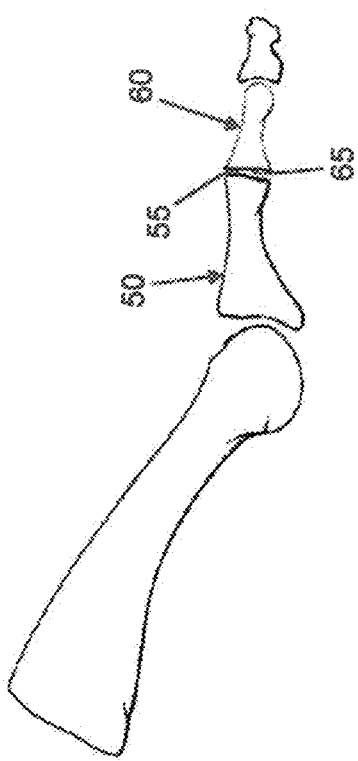

First the distal end of the metatarsal 50 is cut off to correct the deformity and create a bone face 55 suitable for fusion (FIGS. 6 and 7). Then the proximal end of the phalange 60 is removed to correct the deformity and create a bone face 65 suitable for fusion (FIGS. 7 and 8). With these two cuts complete, the bones of the metatarsal-phalange joint can be properly aligned (FIG. 8) for subsequent fusion, as will hereinafter be discussed.

Figure 10:
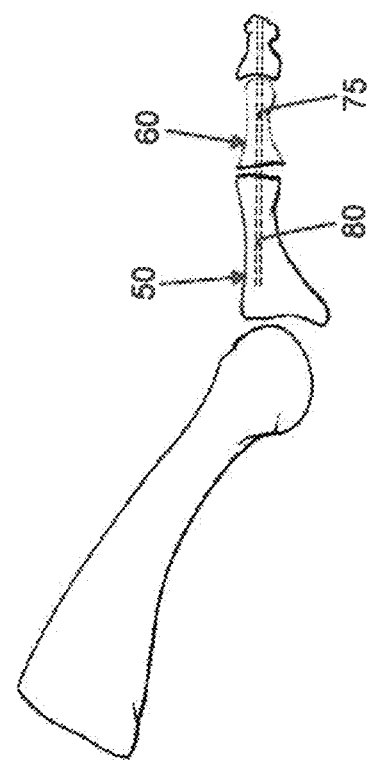
Figure 9:
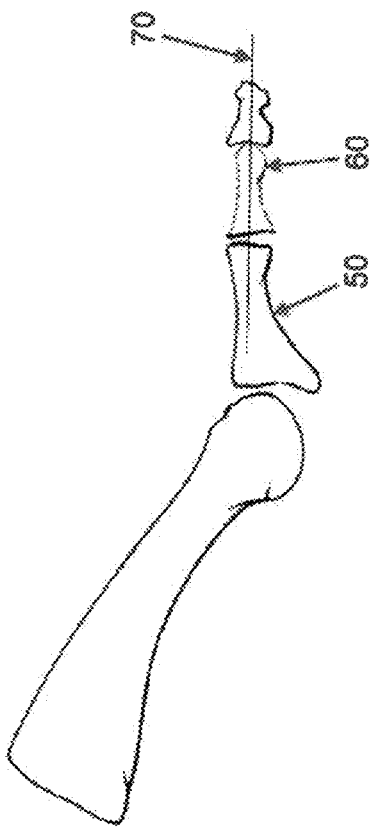

Next, the surgeon inserts a k-wire 70 through the distal end of the toe, phalange 60 and into the metatarsal 50 (FIG. 9). Preferably k-wire 70 passes down the intramedullary canals of phalange 60 and metatarsal 50. Removal of k-wire 70 leaves a canal 75 (i.e., the opened intramedullary canal) in phalange 60 and a canal 80 in metatarsal 50, with canal 75 in phalange 60 being aligned with canal 80 in metatarsal 50 when phalange 60 is aligned with metatarsal 50 (FIG. 10). Canals 75 and 80 receive intramedullary fusion device 5 as will hereinafter be discussed.

Figure 11:
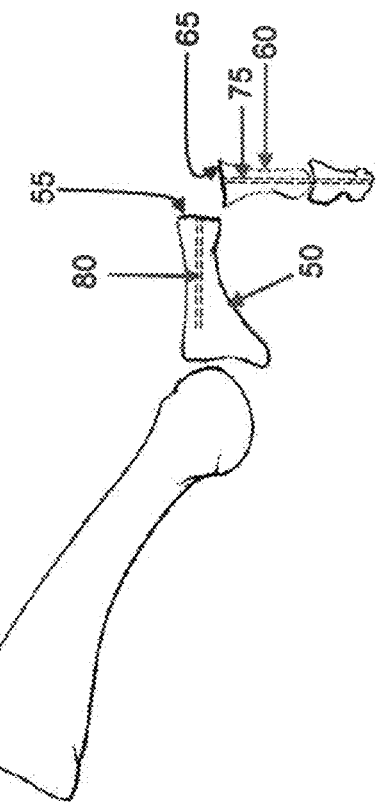

Following removal of k-wire 70, phalange 60 is flexed downward so as to expose the prepared metatarsal face 55 (FIG. 11).

Next, with retaining tabs 30, 40 constraining barbs 25, 35, respectively, of first barbed end region 10 and second barbed end region 15, respectively, to their "inboard" position (i.e., as shown in FIG. 2), intramedullary fusion device 5 has its first barbed end region 10 advanced into canal 80 of metatarsal 50 (FIG. 12). Then removable retaining tab 30 is removed, allowing barbs 25 of first barbed end region 10 to expand outwardly and grip the side wall of canal 80, whereby to securely fasten intramedullary fusion device 5 to metatarsal 50 through an expansive force against the intramedullary surface (FIG. 13). Phalange 60 is then pressed over second barbed region 15 of intramedullary fusion device 5, with second barbed region 15 being received in canal 75 of phalange 60 (FIG. 14). This action brings face 65 of phalange 60 against face 55 of metatarsal 50, with just enough room being left for retaining tab 40 to extend from intramedullary device 5 to a region outside of the bone.

Next, retaining tab 40 is removed so that barbs 35 of second barbed end region 15 are allowed to expand outwardly and grip the side wall of canal 75 of phalange 60 (FIG. 15). At this point barbs 25 of first barbed end region 10 are securely engaging metatarsal 50, and barbs 35 of second barbed end region 15 are securely engaging phalange 60, with central bridge region 20 extending across the fracture line. A force can be applied to reduce any gap left after removing retaining tab 40.

It should be appreciated that novel intramedullary fusion device 5 can first be implanted into phalange 60 and then implanted into metatarsal 50 if the surgeon so chooses.

Figure 15A:
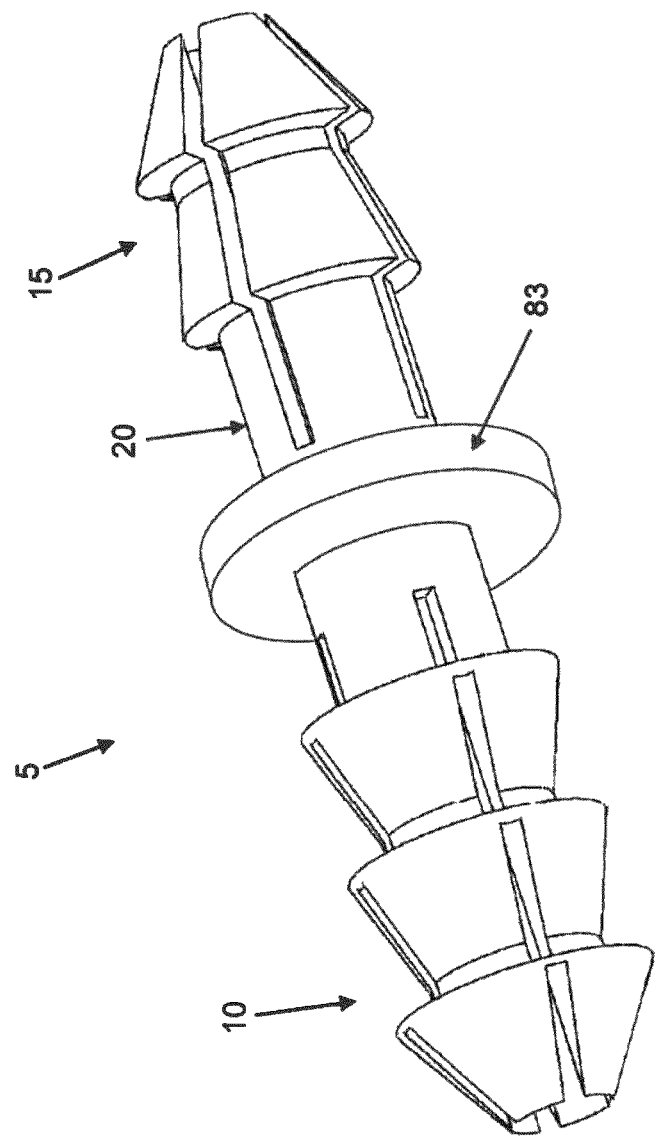
FIG. 15A is a schematic view showing another intramedullary fusion device formed in accordance with the present invention.
Figure 15B:
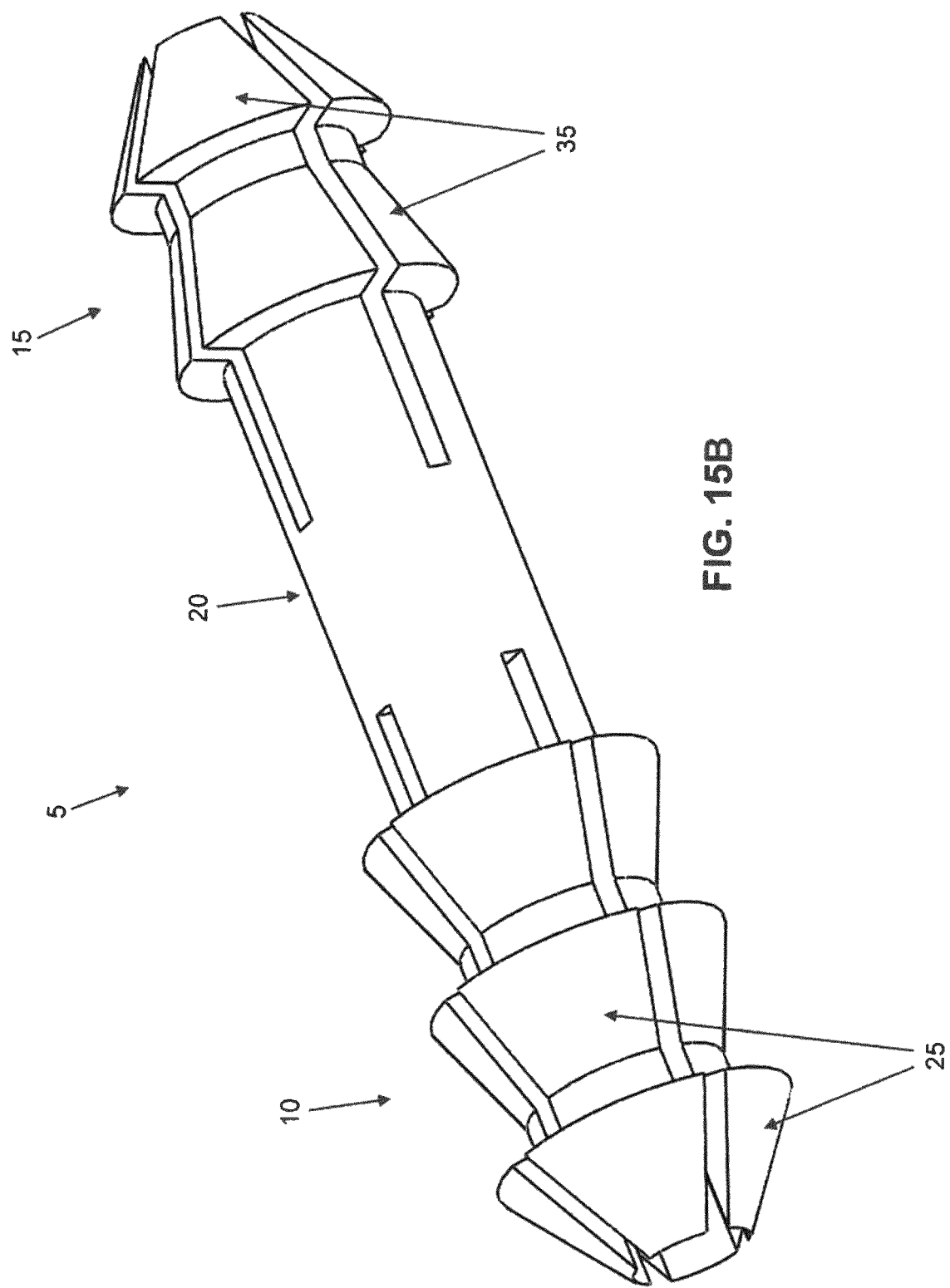
FIG. 15B is a schematic view showing another intramedullary fusion device formed in accordance with the present invention.

If desired, and looking now at FIG. 15A, central bridge region 20 may have an enlargement 83 intermediate its length to act as a stop, limiting how far intramedullary fusion device 5 can be pushed into either side of the intramedullary canal during implantation.

In FIGS. 1-4, barbs 25 of first barbed end region 10 are shown as being circumferentially offset from barbs 35 of second barbed end region 15, i.e., barbs 25 and barbs 35 are not axially aligned with one another. However, if desired, and looking now at FIG. 15B, barbs 25 of first barbed end region 10 may not be circumferentially offset from barbs 35 of second barbed end region 15, i.e., barbs 25 and barbs 35 may be axially aligned with one another in the manner shown in FIG. 15B.

If desired, and looking now at FIGS. 16-18, intramedullary fusion device 5 can have a slight bend from central bridge region 20 to one or both of its first barbed end region 10 and second barbed end region 15. By way of example but not limitation, in the metatarsal-phalange fusion shown in FIGS. 5-15, it may be desirable to provide a slight bend to second barbed end region 15 so as to facilitate the restoration of the normal anatomy. In this form of the invention, intramedullary fusion device 5 may be bent after machining and during the working of the shape memory material, e.g., it may be shape-set at the desired angulation through heat treatment.

It should also be appreciated that the central bridge region 20 can be processed so as to be malleable (i.e., to take a set). At body temperature, the barb regions 10 and 15 can be superelastic while central bridge region 20 can be fully annealed Nitinol or martensitic Nitinol, such that central bridge region 20 is malleable and can take a set. This allows the surgeon to deform central bridge region 20 at the time of surgery so that it assumes the bend desired.

Figure 19:
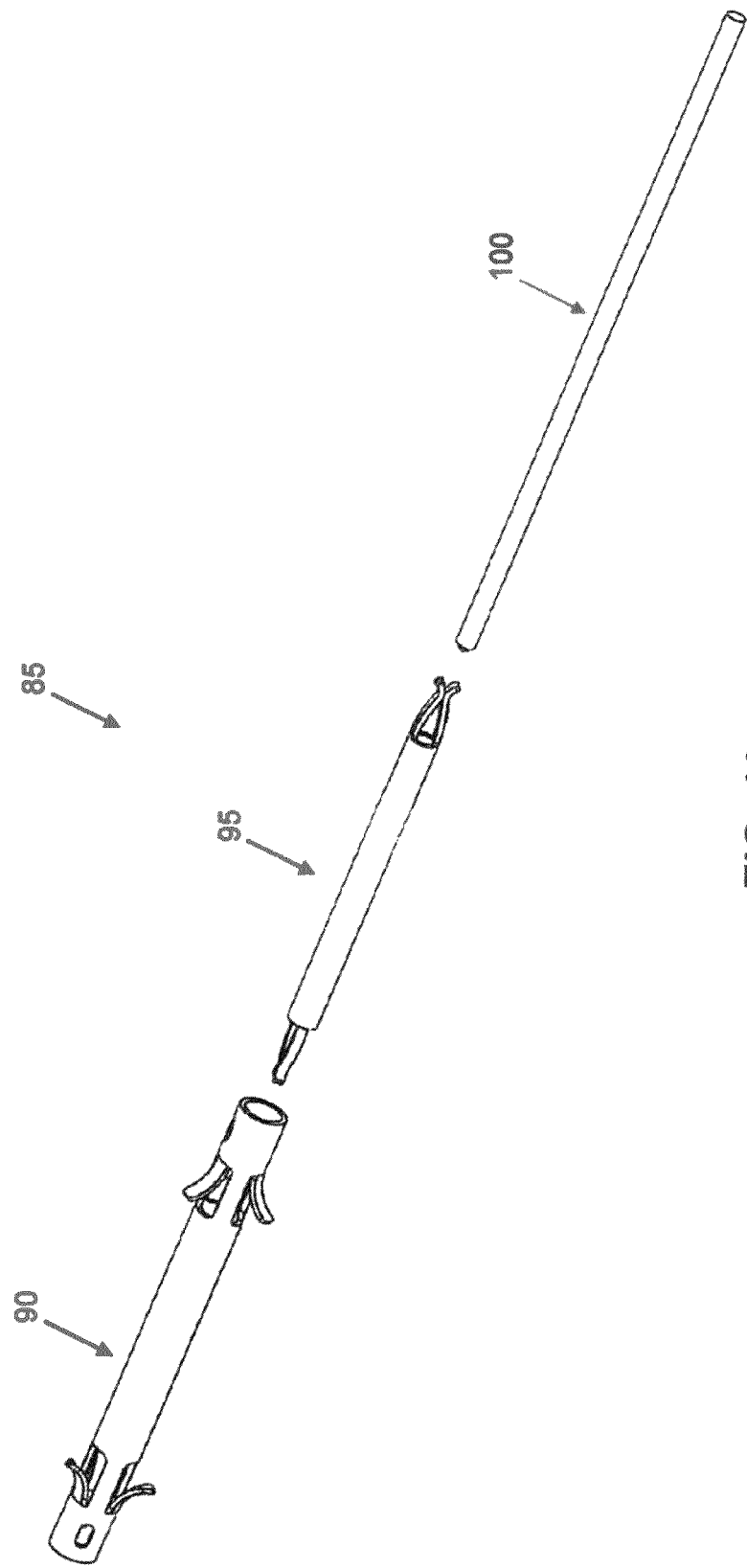
FIGS. 19-25 are schematic views showing an intramedullary fusion system formed in accordance with the present invention.

Looking next at FIG. 19, there is shown an intramedullary fusion system 85 which generally comprises an intramedullary fusion device 90, an internal restrainer 95 and a locking pin 100.

Intramedullary fusion device 90 is manufactured from a shape memory material (e.g., a material capable of exhibiting superelasticity and/or a temperature-induced shape change). The shape memory material may be a metal alloy (e.g., Nitinol) or a polymer (e.g., appropriately processed PEEK). Looking now at FIGS. 20 and 21, intramedullary fusion device 90 comprises a first barbed end region 105, a second barbed end region 110, and a central bridge region 115 connecting first barbed end region 105 and second barbed end region 110. Intramedullary fusion device 90 is preferably cannulated so as to allow the intramedullary fusion device to be installed over a k-wire if desired, while also allowing a k-wire to be passed through the device following implantation if the surgeon desires to fuse a distal or proximal joint. The first and second barbed regions flare outward in multiple planes, preferably engaging the surrounding bone about the full circumference of the intramedullary fusion device, thereby providing excellent torsional stability to the fusion site.

Figure 20:
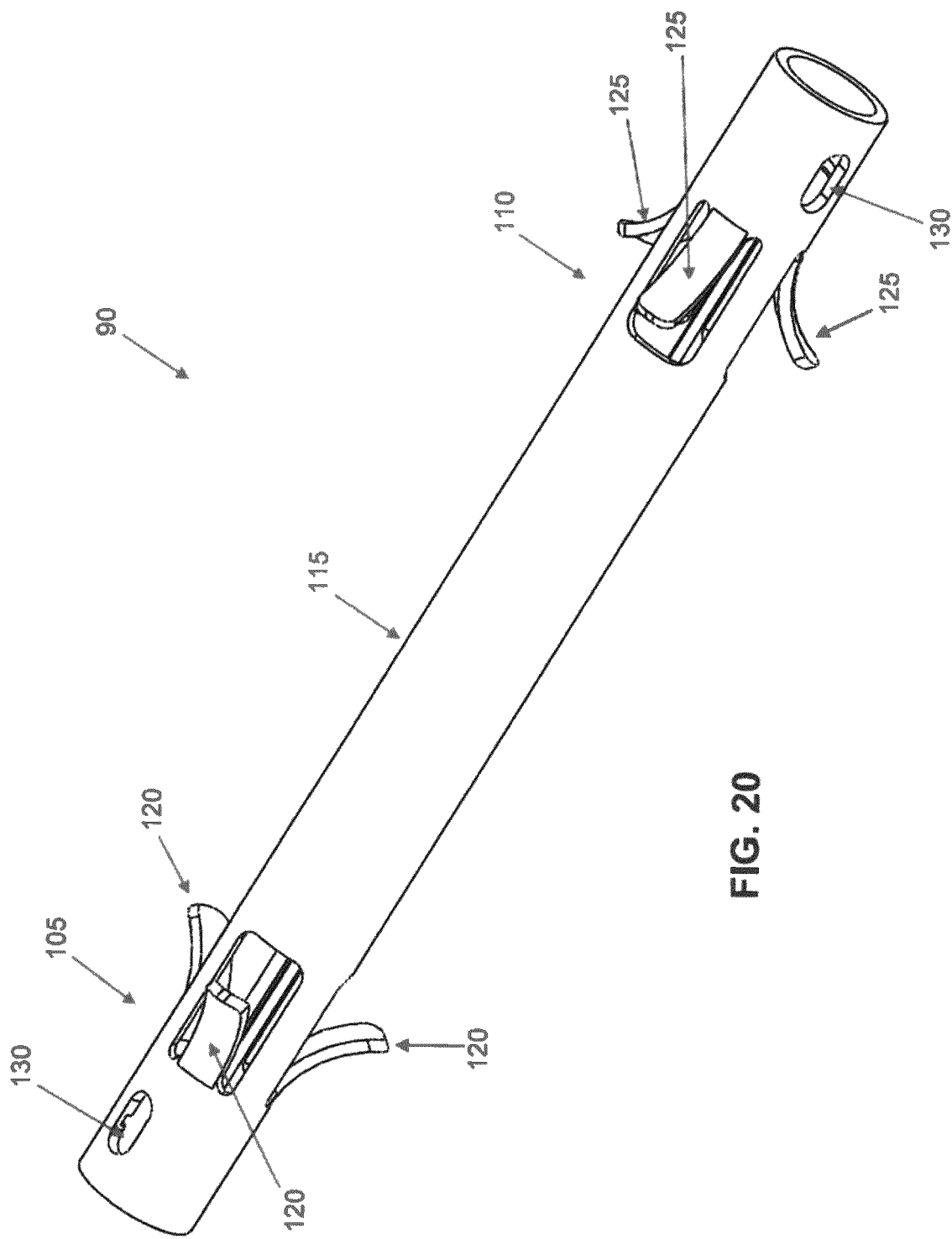
Figure 21:
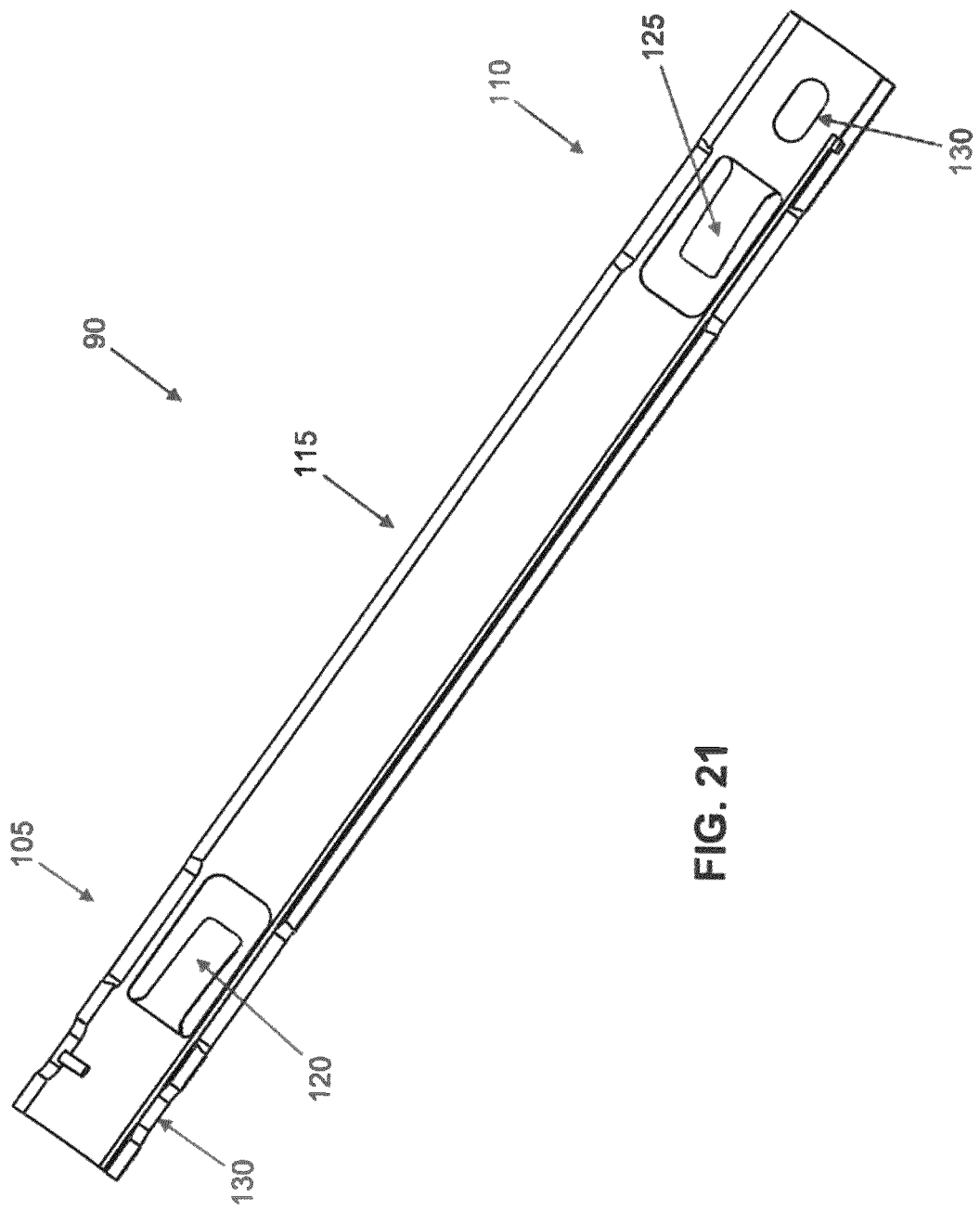

First barbed end region 105 comprises a plurality of barbs 120 which, in their unbiased condition, flare outward from the longitudinal axis of intramedullary fusion device 90 in the manner shown in FIG. 20. The flare may increase linearly over the length of the barb, or it may increase non-linearly over the length of the barb to enable first barbed end region 105 to better engage the "hourglass-shaped"

intramedullary canal. The better that first barbed region 105 engages the intramedullary canal, the more even the pressure distribution will be. While FIG. 20 illustrates a device with four barbs 120 in first barbed end region 105, it should be appreciated that the device can have more or fewer barbs. Barbs 120 can be strained to a position parallel to the longitudinal axis of intramedullary fusion device 90, e.g., during insertion into a hole drilled in bone. Once inserted into the intramedullary canal, barbs 120 flare outwardly so as to engage with the side wall of the drilled hole receiving first barbed end region 105. By angling barbs 120 relative to the longitudinal axis of intramedullary fusion device 90, i.e., with an arrowhead configuration, barbs 120 can ensure that first barbed end region 105 is insertable into a hole in a bone but not withdrawable from the hole in the bone. In this way barbs 120 can selectively lock first barbed end region 105 to a bone fragment, as will hereinafter be discussed.

Second barbed end region 110 comprises a plurality of barbs 125, which, in their unbiased condition, flare outward from the longitudinal axis of intramedullary fusion device 90 in the manner shown in FIG. 20. The flare may increase linearly over the length of the barb, or it may increase non-linearly over the length of the barb to enable second barbed end region 110 to better engage the "hourglass-shaped" intramedullary canal. The better that second barbed region 110 engages the intramedullary canal, the more even the pressure distribution will be. While FIG. 20 illustrates a device with four barbs 125 in second barbed end region 125, it should be appreciated that the device can have more or fewer barbs. Barbs 125 can be strained to a position parallel to the longitudinal axis of intramedullary fusion device 90, e.g., during insertion into a hole drilled in bone, with barbs 125 flaring outwardly so as to remain in constant engagement with the side wall of the drilled hole receiving second barbed end region 110. By angling barbs 125 relative to the longitudinal axis of intramedullary fusion device 90, i.e., with an arrowhead configuration, barbs 125 can ensure that second barbed end region 110 is insertable into a hole in a bone but not withdrawable from the hole in the bone. In this way barbs 125 can selectively lock second barbed end region 110 in the intramedullary canal of a bone fragment, as will hereinafter be discussed.

Note that barbs 120 of first barbed end region 105 are flared in a direction which is opposite to that of barbs 125 of second barbed end region 110.

Central bridge region 115 preferably comprises a generally cylindrical shape and is configured so that it can be selectively strained (i.e., stretched) longitudinally and constrained in that position (e.g., via the aforementioned internal restrainer 95 and locking pin 100). As will hereinafter be discussed, upon removing locking pin 100, internal restrainer 95 will release the constraint on central bridge region 115, whereupon central bridge region 115 will attempt to foreshorten. As will also hereinafter be discussed, this foreshortening can be harnessed to apply compression between two bone fragments.

In order to allow central bridge region 115 to be constrained in its longitudinally stretched state, intramedullary fusion device 90 preferably comprises cutouts 130, disposed in first barbed end region 105 and second barbed end region 110, that allow central bridge region 115 to be constrained in its longitudinally stretched state by internal restrainer 95, as will hereinafter be discussed.

Figure 22:
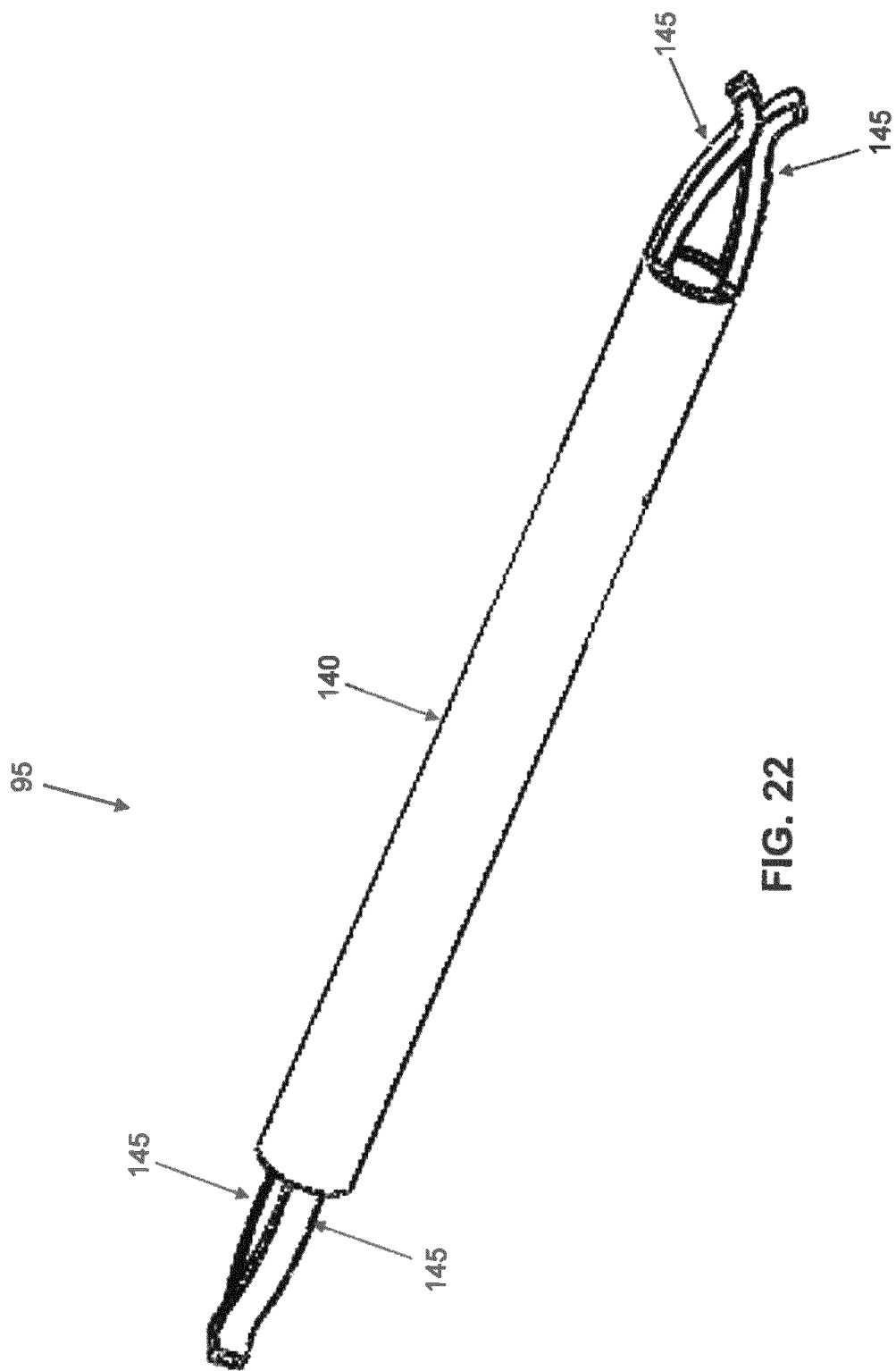

Internal restrainer 95 is shown in further detail in FIG. 22. Internal restrainer 95 may comprise a shape memory material if desired. Internal restrainer 95 generally comprises a cannulated cylindrical body 140 terminating in a pair of fingers 145 at each end of cylindrical body 140. Each pair of fingers 145 are normally biased together, however, they may be elastically forced apart so that they extend outboard beyond the circumference of cylindrical body 140, whereby to allow fingers 145 of internal restrainer 90 to lock to cutouts 130 of intramedullary fusion device 90 when intramedullary fusion device 90 is in its longitudinally stretched state, as will hereinafter be discussed.

Figure 23:
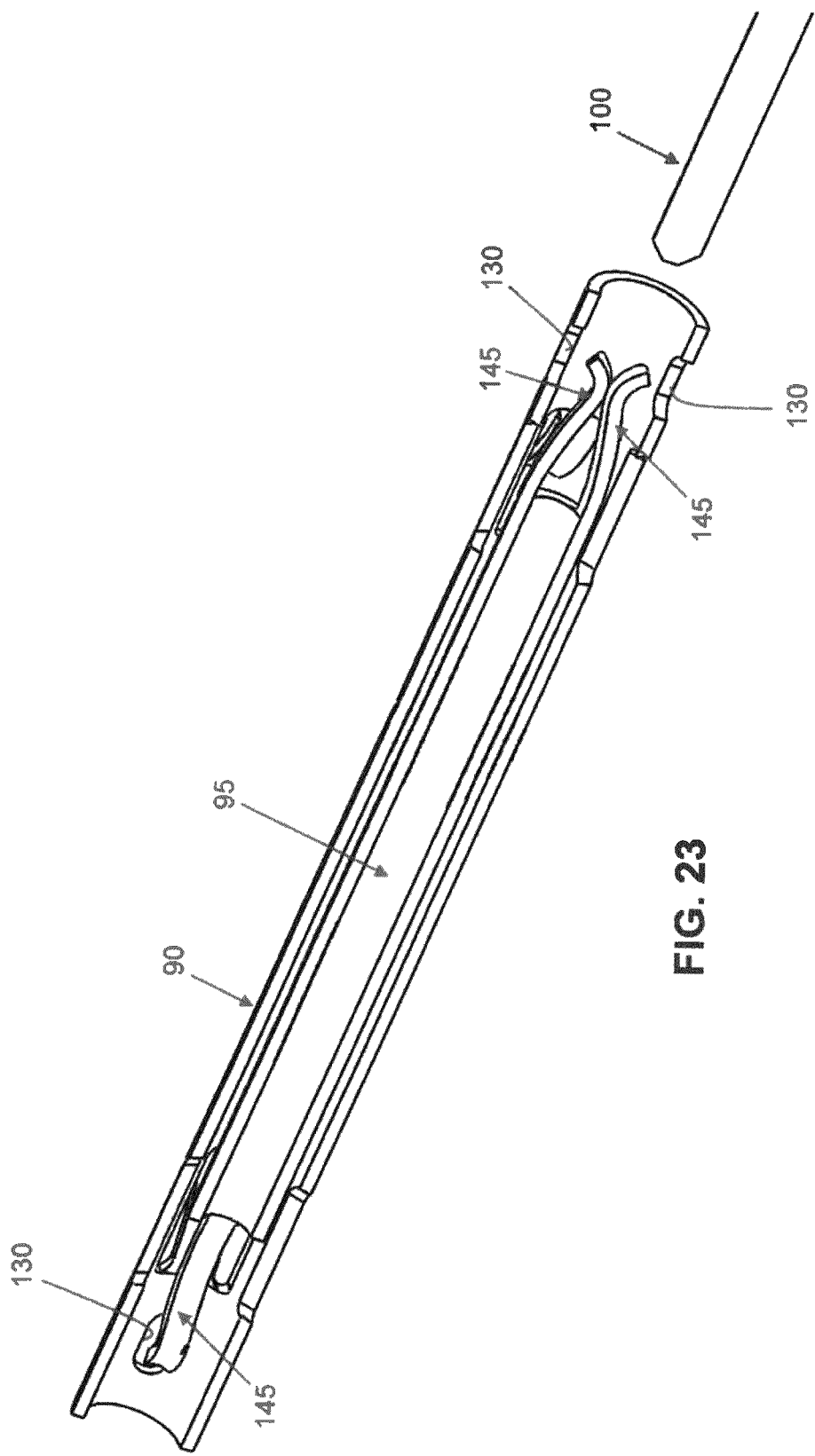
Figure 24:
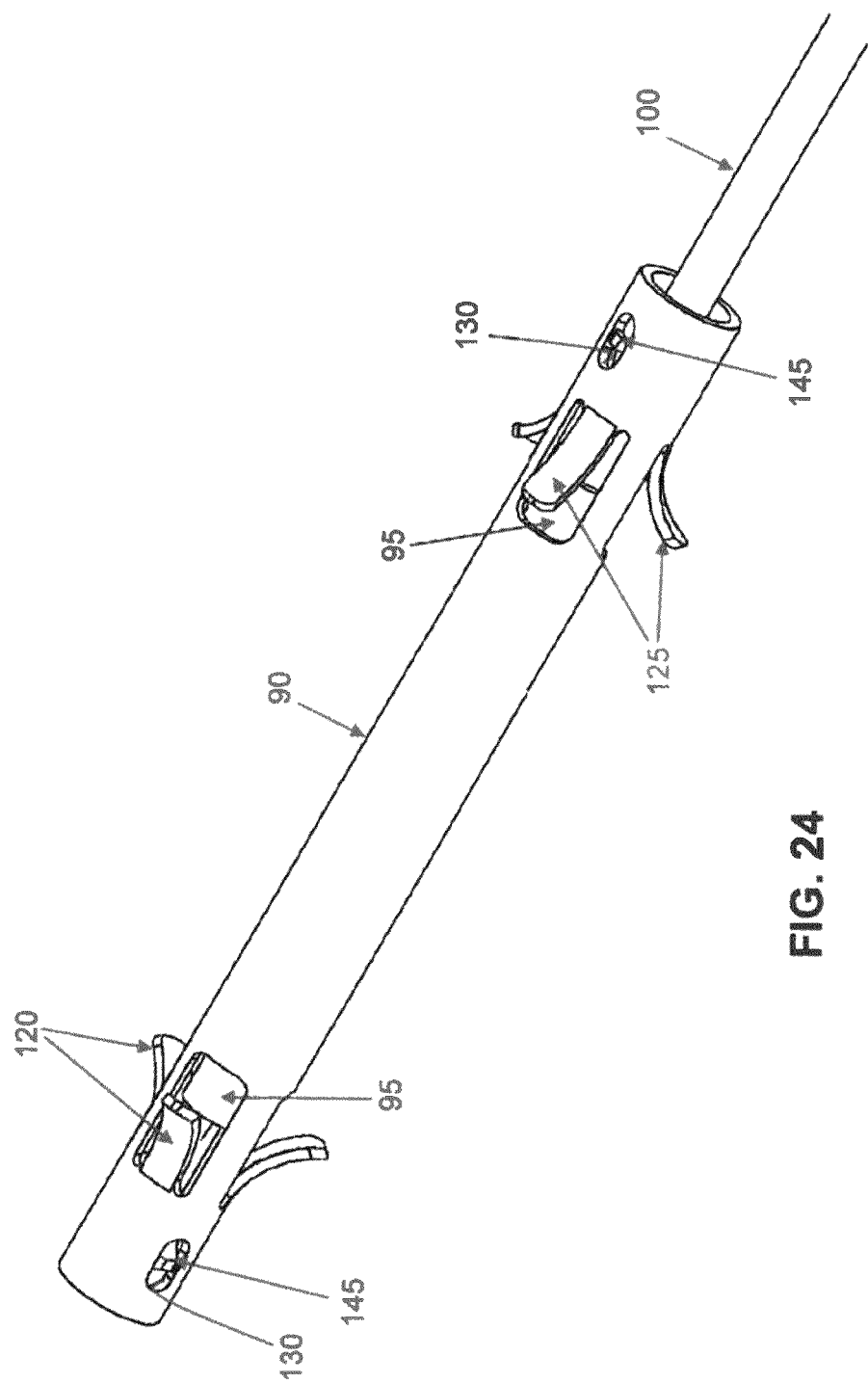
Figure 25:
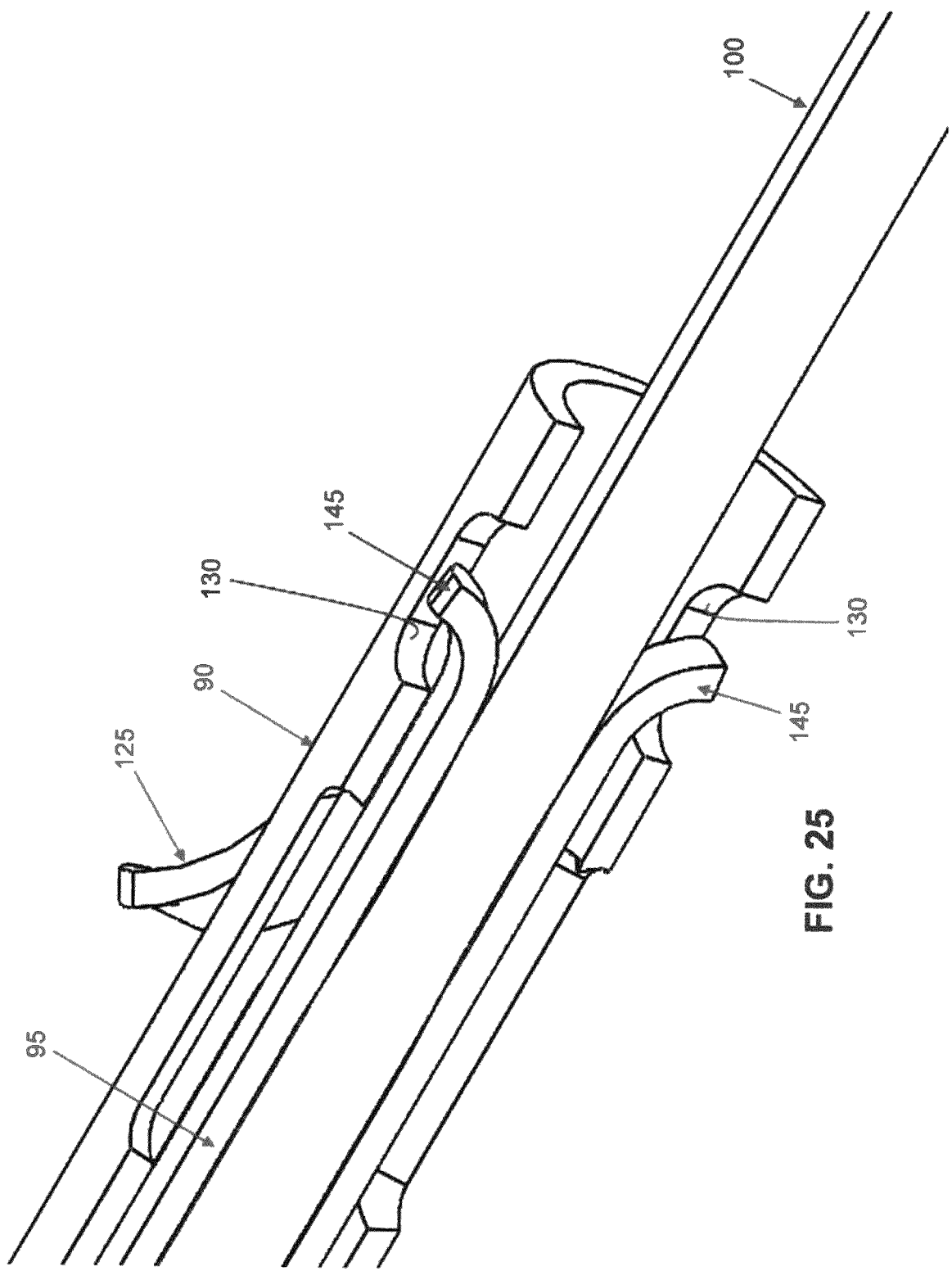

As noted above, central bridge region 115 of intramedullary fusion device 90 can be strained (i.e., longitudinally stretched), locked in that position via internal restrainer 95 and locking pin 100 and, upon removing locking pin 100, internal restrainer 95 will release the constraint on central bridge region 115 of intramedullary fusion device 90, whereupon central bridge region 115 will attempt to foreshorten. More particularly, and looking now at FIGS. 23-25, central bridge region 115 is stretched using a stretching mechanism (not shown) of the sort which will be apparent to those skilled in the art in view of the present disclosure, and internal restrainer 95 is inserted into intramedullary fusion device 90. As internal restrainer 95 is inserted into intramedullary fusion device 90, the pairs of fingers 145 disposed at each end of internal restrainer 95 are aligned with cutouts 130 in first barbed end region 105 and second barbed end region 110. Locking pin 100 is then inserted into internal restrainer 95, whereby to cause the pairs of fingers 145 disposed at each end of internal restrainer 95 to project through cutouts 140 of intramedullary fusion device 90, whereby to lock central bridge region 115 of intramedullary fusion device 90 in its strained (i.e., longitudinally stretched) state. The external load stretching central bridge region 105 (i.e., via the aforementioned stretching mechanism, not shown) can now be removed, and central bridge region 115 of intramedullary fusion device 90 will remain in its strained (i.e., stretched) state due to the action of internal restrainer 95 and locking pin 100. However, when locking pin 100 is thereafter removed from the interior of internal restrainer 95, the pairs of fingers 145 disposed at each end of internal restrainer 95 retract from cutouts 130 by virtue of their inward bias, allowing central bridge region 115 of intramedullary fusion device 90 to foreshorten, whereby to generate compression between the bone fragments, as will hereinafter be discussed.

Figure 26:
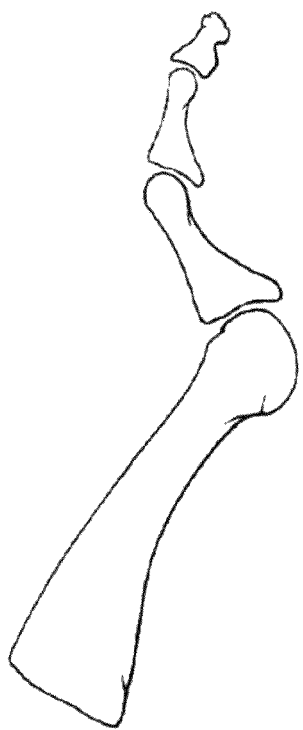
FIGS. 26-36 are schematic views showing the novel intramedullary fusion system of FIGS. 19-25 being used to treat a hammer toe condition.

Intramedullary fusion system 85 may be used to secure together two bone fragments and apply compression to the fracture line. By way of example but not limitation, and looking now at FIGS. 26-36, intramedullary fusion system 85 may be used to treat a hammertoe deformity (FIG. 26).

Figure 27:
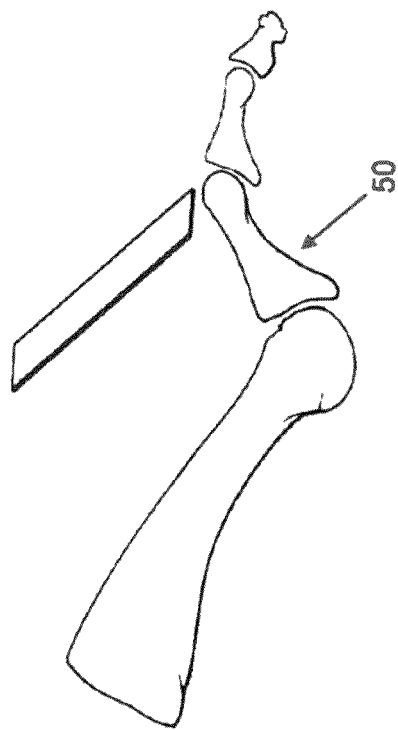
Figure 28:
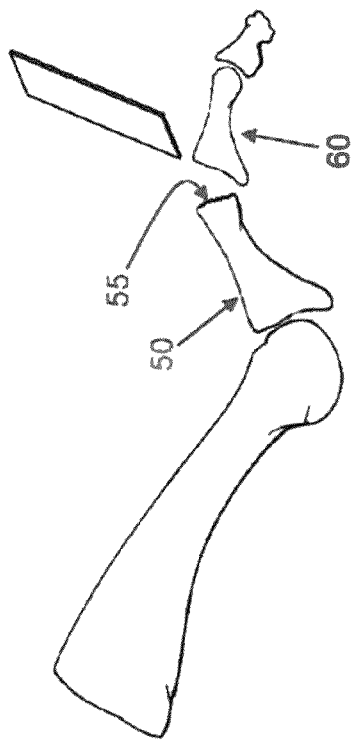
Figure 29:
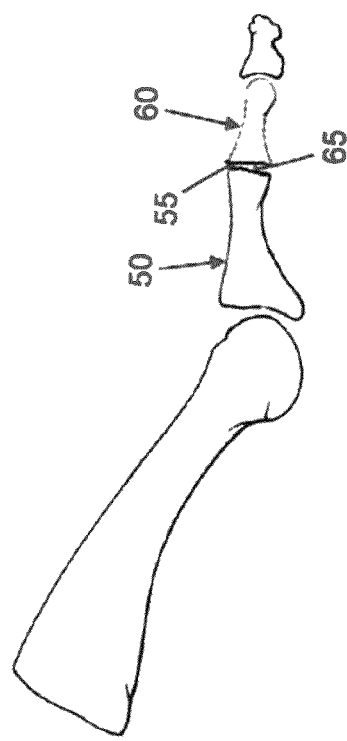

First, the distal end of metatarsal 50 is cut off to correct the deformity and create a bone face 55 suitable for fusion (FIGS. 27 and 28). Then the proximal end of phalange 60 is removed to correct the deformity and create a bone face 65 suitable for fusion (FIGS. 28 and 29). With these two cuts complete, the bones of the metatarsal-phalange joint can be properly aligned (FIG. 29) for subsequent fusion, as will hereinafter be discussed.

Figure 31:
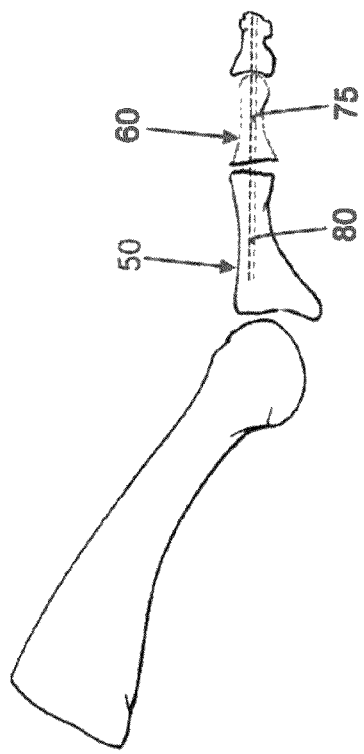
Figure 30:
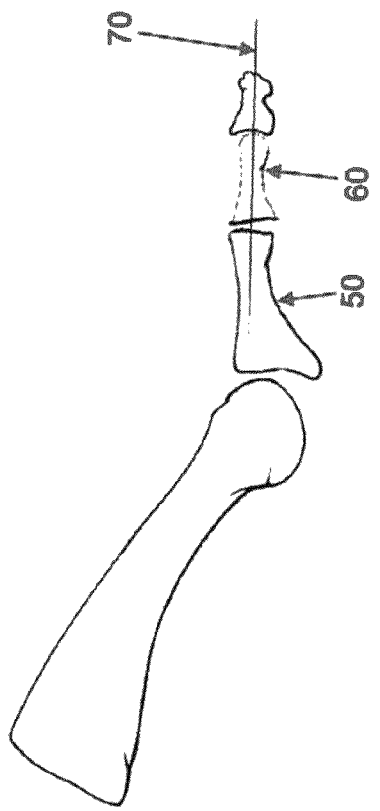

Next, the surgeon inserts k-wire 70 through the distal end of the toe, then through phalange 60 and into metatarsal 50 (FIG. 30). Preferably k-wire 70 passes down the intramedullary canals of phalange 60 and metatarsal 50. Removal of k-wire 70 leaves a canal 75 (i.e., the opened intramedullary canal) in phalange 60 and a canal 80 in metatarsal 50, with canal 75 in phalange 60 being aligned with canal 80 in metatarsal 50 when phalange 60 is aligned with metatarsal 50 (FIG. 31). Canals 75 and 80 receive intramedullary fusion system 85 as will hereinafter be discussed.

Figure 32:
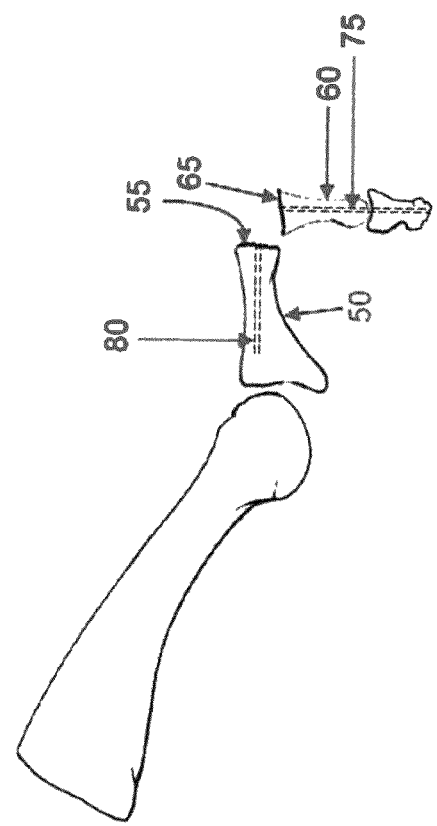

Following removal of k-wire 70, phalange 60 is flexed downward so as to expose the prepared metatarsal face 55 (FIG. 32).

Intramedullary fusion device 90, which has previously been strained (i.e., its central bridge region 115 longitudinally stretched) and locked in this state with internal restrainer 95 and locking pin 100, is then implanted into canal 75 in phalange 60 (FIG. 33), i.e., by advancing the free end of locking pin 100 and second barbed end region 110 of intramedullary fusion device 90 into canal 75 of phalange 60. Note that the flare on barbs 125 of second barbed end region 110 is such that intramedullary fusion device 90 can be advanced into canal 75 of phalange 60 but not withdrawn. Note also that the free end of locking pin 100 extends completely out of phalange 60 and any adjacent bone structure(s) so that it is graspable by the surgeon and able to be retracted when desired through the distal end of the toe.

Figure 34:
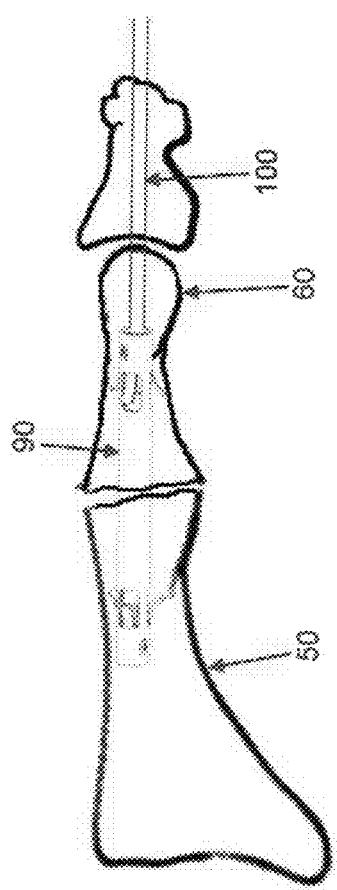

Phalange 60 is then reoriented so that first barbed end region 105 is aligned with canal 80 in metatarsal 50, and then phalange 60 is advanced towards metatarsal 50 so that first barbed end region 105 enters canal 80 of metatarsal 50 (FIG. 34). Note that the flare on barbs 120 of first barbed end region 105 of intramedullary fusion device 90 is such that intramedullary fusion device 90 can be advanced into canal 80 of metatarsal 50 but not withdrawn.

Phalange 60 is advanced towards metatarsal 50 until face 65 of phalange 60 engages face 55 of metatarsal 50. At this point barbs 120 of first barbed end region 105 and barbs 125 of second barbed end region 110 prevent phalange 60 and metatarsal 50 from moving apart.

Figure 36:
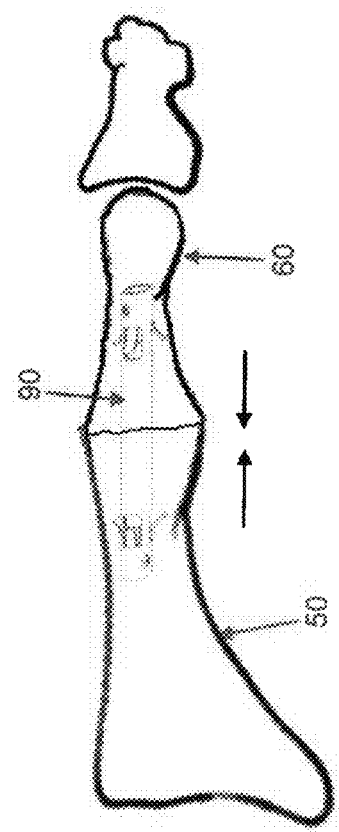
Figure 33:
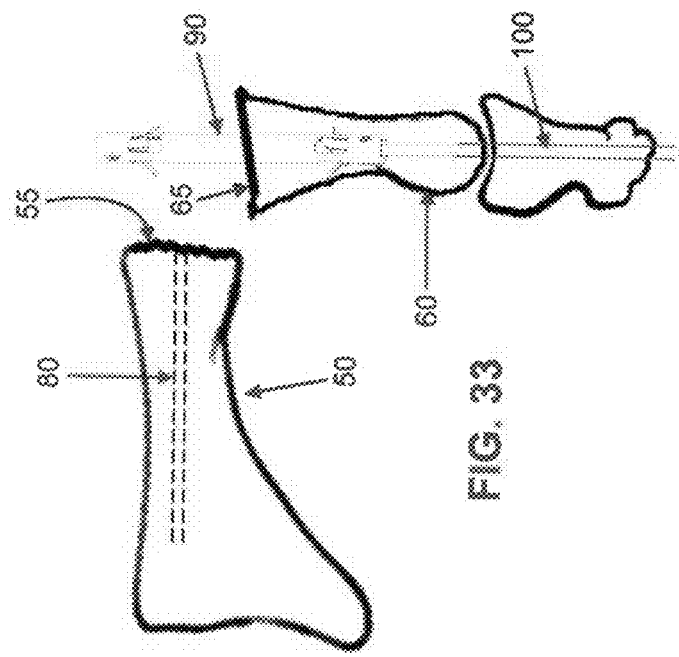
Figure 35:
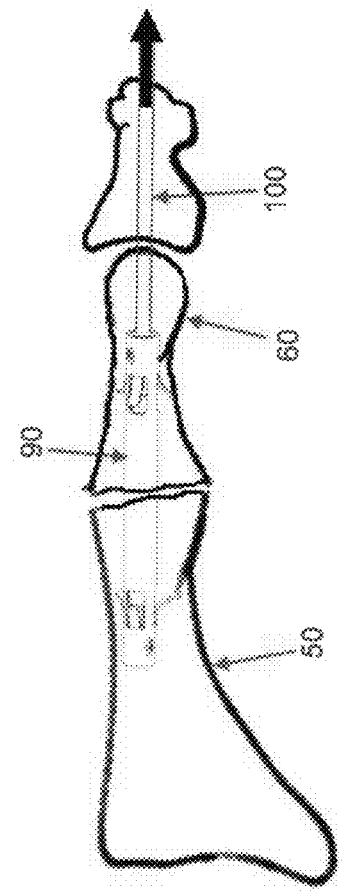

With intramedullary fusion device 90 firmly secured to both phalange 60 and metatarsal 50, locking pin 100 is then removed from internal restrainer 95 (FIG. 35), i.e., by being retracted through the distal end of the toe. This allows the pairs of fingers 145 disposed on each end of internal restrainer 95 to retract from cutouts 130 of intramedullary fusion device 90, which allows central bridge region 115 of intramedullary fusion device 90 to foreshorten, whereby to generate compression between metatarsal 50 and phalange 60 (FIG. 36).

If desired, internal restrainer 95 may be left in place within intramedullary fusion device 90 or, more preferably, internal restrainer 95 may be removed from intramedullary fusion device 90 after intramedullary fusion device 90 has been set, e.g., by grasping internal restrainer 95 with a grasping tool and drawing internal restrainer 95 longitudinally out of intramedullary fusion device 90 and then out canal 75 of phalange 60. Alternatively, internal restrainer 95 can be automatically removed from intramedullary fusion device 90 when locking pin 100 is removed from internal restrainer 95, e.g., by providing the distal end of locking pin 100 and the proximal end of internal restrainer 95 with an appropriate "catch mechanism" so that the retreating locking pin 100 engages internal restrainer 95 and carries internal restrainer 95 out of intramedullary fusion device 90 and then out canal 75 of phalange 60.

If desired, and looking now at FIG. 37, intramedullary fusion device 90 can have a slight bend at one or both of its first barbed end region 105 and second barbed end region 110. By way of example but not limitation, in the metatarsal-phalange fusion shown in FIGS. 26-36, it may be desirable to provide a slight bend to second barbed end region 110 so as to facilitate restoration of the normal anatomy. In this form of the invention, intramedullary fusion device 90 may be bent after machining and during the working of the shape memory material, e.g., it may be shape-set at the desired angulation through heat treatment.

Intramedullary fusion device 90 is specifically engineered so not to "tear through" the bone tissue when central bridge region 115 foreshortens. The compressive forces of intramedullary fusion device 90 can be controlled by modulating the material properties of the intramedullary fusion device and/or the geometry of the intramedullary fusion device.

The percentage of cold work in the shape memory material forming intramedullary fusion device 90 affects the compressive force generated by the intramedullary fusion device. As the percentage of cold work increases, the compression force declines. The intramedullary fusion device should, preferably, have between about 15% and 55% cold work to control the recovery force of the intramedullary device.

Another material property that affects the intramedullary fusion device's compression force is the temperature differential between the body that the intramedullary fusion device will be implanted into (assumed to be 37° C., which is the temperature of a human body) and the austenite finish temperature of the shape memory material forming intramedullary fusion device 90. A smaller temperature differential between the two will result in the intramedullary fusion device generating a small compressive load; conversely, the larger the temperature differential between the two will result in the intramedullary device generating a larger compressive load. The shape memory material that the intramedullary fusion device is made out of should, preferably, have an austenite finish temperature of greater than about −10° C., resulting in a temperature differential of less than about 47° C. when the intramedullary fusion device is implanted (assuming that the intramedullary fusion device is implanted in a human body).

The geometry of the intramedullary fusion device also affects the compression force generated. The cross-sectional area of the hollow central bridge region 115 affects the compression force. As the cross-sectional area increases, so does the compression force that the intramedullary fusion device 90 will generate. In this respect it should be appreciated that it is beneficial for the compression force generated by the foreshortening of intramedullary fusion device 90 to be constant as the bone relaxes and remodels. Thus, the cross-section of hollow central bridge region 115 of intramedullary fusion device 90 preferably has a constant cross-section over its entire length. Cross-sections that are not uniform over the length of hollow central bridge region 115 can result in an increase or decrease in compression as the intramedullary fusion device foreshortens.

The barbs 120, 125 are important for transmitting the compression force to the bone without "tearing through" the bone. The height, width, and number of barbs 120, 125 on the intramedullary device 90 are all important to the intramedullary device's ability to not "tear through" the bone.

It should also be appreciated that shape memory material can be processed to exhibit two-way shape memory. The intramedullary fusion device 90 can be trained to have an austenitic shape (i.e., barbs expanded) and a martensitic shape (i.e., barbs extending parallel to the longitudinal axis of intramedullary fusion device 90). In this case, the barbs can be in their austenitic shape at about body temperature. The barbs can be deformed via the creation of stress induced martensite to implant the intramedullary fusion device. If the intramedullary fusion device thereafter needs to be removed, the intramedullary fusion device may be cooled (e.g., with cold saline) to a temperature below the austenite start temperature of the shape memory material, and more preferably below the martensite start temperature of the shape memory material, and most preferably below the martensite finish temperature of the shape memory material. When cooled, the intramedullary fusion device 90 will take on its martensitic shape (i.e., the barbs laying parallel to the longitudinal axis of the intramedullary fusion device), and the surgeon can easily remove the intramedullary fusion device.

Additionally, the intramedullary fusion device can be made such that central bridge region 115 of intramedullary fusion device 90 has one austenite start temperature, and such that barbs 120, 125 have a lower austenite start temperature. Thus, the intramedullary fusion device can be stretched at a temperature less than the austenite start temperature of central bridge region 115 but above the austenite start temperature of barbs 120, 125. Thus barbs 120, 125 will be in the austenite phase and able to undergo a stress induced martensite transformation during insertion of intramedullary fusion device 90 into a bone canal. Maintaining the intramedullary fusion device at a temperature below the austenite start temperature of central bridge region 115 allows the intramedullary fusion device to remain in its elongated state. The intramedullary fusion device can then be advanced into a bone canal as discussed above. When the central bridge region 115 warms (either to body temperature, or to a temperature above body temperature, e.g., through the application of warm saline), central bridge region 115 will foreshorten, generating and maintaining compression across the fracture line.

It should also be appreciated that central bridge region 115 of intramedullary fusion device 90 can be processed so as to be malleable (i.e., to take a set). At body temperature, first barbed end region 105 and second barbed end region 110 can be superelastic while central bridge region 115 can be fully annealed Nitinol or martensitic Nitinol. This allows the surgeon to deform the implant at the time of surgery to the bend desired.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An intramedullary device comprising:
   a) a central bridge region having a first end and a second end along a longitudinal axis, wherein the central bridge region is cylindrical and has a length extending along the longitudinal axis and a diameter, wherein the length is greater than the diameter;
   b) a bone engaging feature at both the first end and the second end, wherein at least one bone engaging feature comprises a first barb and a second barb which, in an unbiased condition, flare outwardly from the longitudinal axis of the central bridge region and which are capable of being elastically constrained to a constrained condition such that the first end of the central bridge region may be advanced into a hole in a first bone fragment when the first barb and the second barb are elastically constrained, and the first barb and the second barb are prevented from being withdrawn from the hole in the first bone fragment when the first barb and the second barb are not constrained;
   c) a removable retaining tab for elastically constraining the first barb and the second barb of the at least one bone engaging feature, wherein the removable retaining tab slides relative to the longitudinal axis of the central bridge region to allow the first barb and the second barb of the at least one bone engaging feature to move from the constrained condition to the unbiased condition, and the removeable retaining tab partially surrounds a circumference of the at least one bone engaging feature when in the constrained condition,
   wherein the first barb and the second barb of the at least one bone engaging feature combine to form a substantially continuous extension of the central bridge region when the first barb and the second barb are elastically constrained, wherein movement of the first barb of the at least one bone engaging feature from the constrained condition to the unbiased condition occurs within a first plane, and movement of the second barb of the at least one bone engaging feature from the constrained condition to the unbiased condition occurs within a second plane, and the first plane intersects the second plane,
   wherein the removable retaining tab comprises a first removable retaining tab and a second removable retaining tab, and the first removable retaining tab constrains one of the bone engagement features at the first end, and the second removable retaining tab constrains the other of the bone engagement features at the second end, and
   wherein the device i) is cannulated, ii) generates a compressive load, and iii) comprises nitinol.

2. The intramedullary device according to claim 1 wherein both of the bone engaging features comprise the first barb and the second barb.

3. The intramedullary device according to claim 1 wherein the device is cannulated along the longitudinal axis along an entire length of the central bridge region.

4. The intramedullary device according to claim 1 wherein the first barb and the second barb each include a plurality of barbed segments.

5. The intramedullary device according to claim 1 wherein the first removable retaining tab and the second removable retaining tab are separately detachable from the intramedullary device.

6. An intramedullary device comprising:
   a) a central bridge region having a first end and a second end along a longitudinal axis;
   b) a bone engaging feature at both the first end and the second end, wherein both of the bone engaging features comprise a first barb and a second barb which, in an unbiased condition, flare outwardly from the longitudinal axis of the central bridge region and which are capable of being elastically constrained to a constrained condition such that the first end of the central bridge region may be advanced into a hole in a first bone fragment when the first barb and second barb of both of the bone engaging features are elastically constrained, and the first barb and second barb of both of the bone engaging features are prevented from being withdrawn from the hole in the first bone fragment when the first barb and the second barb of both of the bone engaging features are not constrained; and
   c) a removable retaining tab for elastically constraining the first barb and the second barb of at least one of the bone engaging features, wherein the removable retaining tab slides relative to the longitudinal axis of the central bridge region to allow the first barb and the second barb of the at least one of the bone engaging features to move from the constrained condition to the unbiased condition, wherein the removeable retaining tab partially surrounds a circumference of the at least one of the bone engaging features when in the constrained condition, and the removable retaining tab comprises a first removable retaining tab and a second removable retaining tab, and the first removable retaining tab constrains the bone engagement feature at the first end, and the second removable retaining tab constrains the bone engagement feature at the second end wherein the device i) is cannulated along the longitudinal axis, ii) generates a compressive load, and iii) comprises nitinol.

7. The intramedullary device according to claim 6 wherein the central bridge region is cylindrical.

8. The intramedullary device according to claim 6 wherein the central bridge region is malleable.

9. The intramedullary device according to claim 8 wherein movement of the first barb of both the bone engaging features from the constrained condition to the unbiased condition occurs within a first plane, and movement of the second barb of both the bone engaging features from the constrained condition to the unbiased condition occurs within a second plane.

10. The intramedullary device according to claim 9 wherein the first plane intersects the second plane.

11. The intramedullary device according to claim 8 wherein one of the bone engaging features includes a third barb.

12. The intramedullary device according to claim 11 wherein movement of the first barb and the third barb of the one of the bone engaging features from the constrained condition to the unbiased condition occurs within a first plane, and movement of the second barb of the one of the bone engaging features from the constrained condition to the unbiased condition occurs within a second plane.

13. The intramedullary device according to claim 12 wherein the first plane intersects the second plane.

14. The intramedullary device according to claim 11 wherein the one of the bone engaging features includes a fourth barb.

15. The intramedullary device according to claim 14 wherein movement of the first barb and the third barb of the one of the bone engaging features from the constrained condition to the unbiased condition occurs within a first plane, and movement of the second barb and the fourth barb of the one of the bone engaging features from the constrained condition to the unbiased condition occurs within a second plane.

16. The intramedullary device according to claim 15 wherein the first plane intersects the second plane.

17. The intramedullary device according to claim 16 wherein the first plane is perpendicular to the second plane.

18. The intramedullary device according to claim 6 wherein at least one of the bone engaging features is laterally aligned with the longitudinal axis of the central bridge region.

19. The intramedullary device according to claim 6 wherein at least one of the bone engaging features is laterally offset from the longitudinal axis of the central bridge region.

20. The intramedullary device according to claim 6 wherein the first barb and the second barb of at least one of the bone engaging features combine to form a substantially continuous extension of the central bridge region when the first barb and the second barb are elastically constrained.

21. The intramedullary device according to claim 6 wherein an end of at least one of the first barb and the second barb of at least one of the bone engaging features includes an edge.

22. The intramedullary device according to claim 6 wherein the central bridge region has a length extending along the longitudinal axis and a diameter, and the length is greater than the diameter.

23. The intramedullary device according to claim 6 wherein the device is cannulated along an entire length of the central bridge region.

24. The intramedullary device according to claim 6 wherein the first barb and the second barb each include a plurality of barbed segments.

25. The intramedullary device according to claim 2 wherein the first removable retaining tab and the second removable retaining tab are separately detachable from the intramedullary device.

26. An intramedullary device comprising:
 a) a central bridge region having a first end and a second end along a longitudinal axis;
 b) a bone engaging feature at both the first end and the second end, wherein both of the bone engaging features comprise a first barb and a second barb which, in an unbiased condition, flare outwardly from the longitudinal axis of the central bridge region and which are capable of being elastically constrained to a constrained condition such that the first end of the central bridge region may be advanced into a hole in a first bone fragment when the first barb and second barb of both of the bone engaging features are elastically constrained, and the first barb and second barb of both of the bone engaging features are prevented from being withdrawn from the hole in the first bone fragment when the first barb and the second barb of both of the bone engaging features are not constrained; and
 c) a removable retaining tab for elastically constraining the first barb and the second barb of the bone engaging feature at the first end of the central bridge region, wherein the removable retaining tab slides relative to the longitudinal axis of the central bridge region to allow the first barb and the second barb of the bone engaging feature at the first end to move from the constrained condition to the unbiased condition, and the removeable retaining tab partially surrounds a circumference of the bone engaging feature at the first end when in the constrained condition, wherein movement of the first barb of the bone engaging feature at the first end from the constrained condition to the unbiased condition occurs within a first plane, and movement of the second barb of the bone engaging feature at the first end from the constrained condition to the unbiased condition occurs within a second plane,
 wherein the removable retaining tab comprises a first removable retaining tab and a second removable retaining tab, and the first removable retaining tab constrains the bone engagement feature at the first end, and the second removable retaining tab constrains the bone engagement feature at the second end, and
 wherein the device i) is cannulated, ii) generates a compressive load, and iii) comprises nitinol.

27. The intramedullary device according to claim 26 wherein the first removable retaining tab and the second removable retaining tab are separately detachable from the intramedullary device.

* * * * *